(12) United States Patent
Avni

(10) Patent No.: US 10,668,231 B2
(45) Date of Patent: Jun. 2, 2020

(54) DRUG DELIVERY DEVICE

(75) Inventor: Yuval Avni, Tel-Aviv (IL)

(73) Assignee: RESPINOVA LTD., Herzliya Pituach (IL)

( * ) Notice: Subject to any disclaimer, the term of this patent is extended or adjusted under 35 U.S.C. 154(b) by 647 days.

(21) Appl. No.: 13/512,766

(22) PCT Filed: Dec. 2, 2010

(86) PCT No.: PCT/IL2010/001017
§ 371 (c)(1),
(2), (4) Date: Jun. 4, 2012

(87) PCT Pub. No.: WO2011/067763
PCT Pub. Date: Jun. 9, 2011

(65) Prior Publication Data

US 2012/0247466 A1 Oct. 4, 2012

Related U.S. Application Data

(60) Provisional application No. 61/265,775, filed on Dec. 2, 2009.

(51) Int. Cl.
*A61M 15/00* (2006.01)
*A61M 16/00* (2006.01)
*A61M 16/10* (2006.01)

(52) U.S. Cl.
CPC ...... *A61M 15/0065* (2013.01); *A61M 15/002* (2014.02); *A61M 15/0003* (2014.02); *A61M 15/0016* (2014.02); *A61M 15/0035* (2014.02); *A61M 15/0086* (2013.01); *A61M 15/009* (2013.01); *A61M 16/0006* (2014.02); *A61M 2016/0021* (2013.01); *A61M 2016/0039* (2013.01); *A61M 2016/103* (2013.01);
(Continued)

(58) Field of Classification Search
CPC .............. A61M 15/08; A61M 15/0091; A61M 15/0093; A61M 15/0095; A61M 15/0096; A61M 15/0098; A61M 16/00; A61M 15/0065; A61M 15/0003; A61M 15/0016; A61M 15/002; A61M 15/0035; A61M 15/0086; A61M 15/009; A61M 2016/0021; A61M 2016/0039; A61M 2016/1025; A61M 2016/103; A61M 2205/103; A61M 2230/432; A61M 2230/435
USPC .............. 128/200.11–200.24, 203.12, 203.15
See application file for complete search history.

(56) References Cited

U.S. PATENT DOCUMENTS 6,880,555 B1 4/2005 Brunnberg et al.
2002/0033176 A1* 3/2002 Casper .............. A61M 15/0028
128/203.15

(Continued)

*Primary Examiner* — Gregory Anderson
*Assistant Examiner* — Elliot S Ruddie

(57) ABSTRACT

The present invention discloses a device useful for facilitating delivery of drugs or medicaments to the respiratory system of a user. The device comprising a mechanism for interrupting the airflow during inhalation or exhalation performed by the user through the device by generating pressure pulses within the respiratory system of the user, such that the delivery of the drugs to the user is facilitated; the pressure pulses are selected from the group consisting of: inspiratory Negative Pressure (NP) pulses, inspiratory Positive Pressure (PP) pulses, expiratory Negative Pressure (NP) pulses, expiratory Positive Pressure (PP) pulses into the respiratory system, and any combination thereof.

10 Claims, 40 Drawing Sheets

(52) U.S. Cl.
CPC ............... *A61M 2016/1025* (2013.01); *A61M 2205/103* (2013.01); *A61M 2230/432* (2013.01); *A61M 2230/435* (2013.01)

(56) References Cited

U.S. PATENT DOCUMENTS

| | | | |
|---|---|---|---|
| 2004/0216741 A1* | 11/2004 | Arnott | 128/204.18 |
| 2005/0005933 A1 | 1/2005 | Seppala et al. | |
| 2008/0156319 A1 | 7/2008 | Avni | |
| 2008/0200848 A1 | 8/2008 | Avni | |
| 2008/0257358 A1 | 10/2008 | Stern et al. | |
| 2008/0264416 A1* | 10/2008 | Gonda et al. | 128/203.15 |

* cited by examiner

DRUG DELIVERY DEVICE

FIELD OF THE INVENTION

The purpose of this invention is to provide a device and method for drug delivery to the respiratory system.

BACKGROUND

Manifold devices and methods of delivering droplets or particles of drugs to the respiratory system, especially the lungs have been proposed. In many of these devices, the aforementioned droplets or particles are picked up due to the Venturi effect as the airstream passes over the drug supply on its way into the respiratory system. Contemporary devices suffer from several drawbacks, including the very low ratio of drug that reaches its target location (e.g. the terminal bronchioles and alveoli); and the skill and cooperation required from the patient using the device. It would be highly advantageous to provide a method of improving the delivery of the aforementioned droplets or particles to the target tissues, such as the alveolar walls of the lungs, to ensure better uptake of the drugs. Moreover, it would also be highly advantageous to prepare the lungs prior to drug dispersion for optimal drug uptake.

SUMMARY

The invention delivers a stream of fluid that is periodically stopped by means of a valve. When a person breathes freely, normal negative pressure (NNP) is created within the airways during inhalation. A user inhaling the abovementioned stream of fluid will experience periods of relatively high negative pressure during those periods when the supply of fluid is stopped. These periods of high negative pressure have beneficial effects for various disorders and also facilitate the delivery of any drugs or medicaments in the fluid flow.

An additional effect of pulsating negative pressure prepares the lungs for improved drug uptake. Additionally, this invention creates alternating pulses of positive pressure and negative pressure. Additionally, this invention provides devices and methods for drug delivery to the sinuses.

It is one object of the present invention to disclose a device useful for facilitating delivery of drugs or medicaments to the respiratory system of a user. The device comprises a mechanism for interrupting the airflow during inhalation or exhalation performed by the user through the device by generating pressure pulses within the respiratory system of the user, such that the delivery of the drugs to the user is facilitated; the pressure pulses are selected from the group consisting of: inspiratory Negative Pressure (NP) pulses, inspiratory Positive Pressure (PP) pulses, expiratory Negative Pressure (NP) pulses, expiratory Positive Pressure (PP) pulses into the respiratory system, and any combination thereof.

It is another object of the present invention to disclose the device as define above, wherein the device is adapted for delivering the drugs to the upper respiratory tract of the respiratory system.

It is another object of the present invention to disclose the device as define above, wherein the device is adapted for delivering drugs to the lower respiratory tract of the respiratory system.

It is another object of the present invention to disclose a device useful for delivering drugs to the respiratory system of a user. The device comprises:

a. an air controlling mechanism for controlling passage of air during inhalation or exhalation of the air;
b. at least one container for storing the drugs;
c. a drug releasing mechanism for delivering the drugs from the container to the user;

It is within the scope of the present invention that the air controlling mechanism is adapted to generate pressure pulses of Negative Pressure and/or Positive Pressure into the respiratory system during inspiration and/or expiration, and the drug releasing mechanism is adapted for entraining the drugs into the pressure pulses, such that uptake of the drugs by the tissues of the respiratory system is facilitated; the pressure pulses are selected from the group consisting of: inspiratory Negative Pressure (NP) pulses, inspiratory Positive Pressure (PP) pulses, expiratory Negative Pressure (NP) pulses, expiratory Positive Pressure (PP) pulses into the respiratory system, and any combination thereof.

It is another object of the present invention to disclose the device as define above, wherein the air controlling mechanism comprises means for forcing a stream of fluid towards the patient's respiratory system.

It is another object of the present invention to disclose the device as define above, wherein the device is adapted for delivery of powdered drug supplied in capsule form.

It is another object of the present invention to disclose the device as define above, wherein the air controlling mechanism comprises a shutter for interrupting the stream of air during patient's inspiration or expiration, such that a pulse of Negative Pressure is induced within the patient's respiratory system.

It is another object of the present invention to disclose the device as define above, wherein the shutter comprises a perforated rotating disc adapted to allow passage of the air through the perforation within the disc and to block and unblock the passage of the air.

It is another object of the present invention to disclose the device as define above, wherein the air controlling mechanism comprises a motor driven disc wheel adapted for synchronization with the drug releasing mechanism.

It is another object of the present invention to disclose the device as define above, wherein the drug releasing mechanism is adapted to be opened by a drop in pressure during inhalation and closed by a rise in pressure during exhalation.

It is another object of the present invention to disclose the device as define above, wherein the drug releasing mechanism comprises a drug releasing shutter for controlling release of the drugs from the container during the operation of the air controlling mechanism.

It is another object of the present invention to disclose the device as define above, wherein the device additionally comprises fluid vibrating means 26 (FVM) for vibrating the medication and the air to facilitate drug delivery, the FVM selected from the group comprising an acoustic means mechanical means or electromechanical (piezoelectric) means.

It is another object of the present invention to disclose the device as define above, wherein the FVM is located in the middle section of the device or proximally to the outlet of the container.

It is another object of the present invention to disclose the device as define above, wherein the container comprises a pressure generator for generating high pressure therein.

It is another object of the present invention to disclose the device as define above, wherein the device is pocket sized device.

It is another object of the present invention to disclose the device as define above, wherein the device is characterized by a non-drug mode in which the drug releasing mechanism does not provide drugs, and solely controls the passage of air during inhalation or exhalation of the air.

It is another object of the present invention to disclose the device as define above, wherein the device is adapted for use a s a sinusitis inhaler for use with one or both nostrils.

It is another object of the present invention to disclose the device as define above, further comprising a ratchet and pawl mechanism adapted to activate the device by lifting a pawl by the user's teeth.

It is another object of the present invention to disclose the device as define above, further comprising spirometric, chemical or other types of sensors adapted to measure parameters of the user's breath and to modify the treatment protocols of the device via a feedback mechanism, said sensors are adapted to measure parameters selected from the group consisting of: peak flow, flow rate, FEV1, spirometric parameters, inhalation pressure, exhalation pressure, inspiratory pressure, expiratory pressure, vital capacity, inhaled $CO_2$ concentration, exhaled $CO_2$ concentration, inhaled $O_2$ concentration, exhaled $O_2$ concentration, and any combination thereof.

It is another object of the present invention to disclose the device as define above, wherein the device additionally comprises means for pulling the lower jaw forward with respect to the upper jaw such that the geometry of the upper airway facilitates smooth flow of air and drug into the lungs.

It is another object of the present invention to disclose the device as define above, wherein the drugs are selected from the group consisting of: vaporized essential oils, volatile compounds, etheric oils, terepenes, terpanols and either water miscible or water-immiscible extracts, especially oils or extracts obtained from *Amyris*, Balsam, Bay Rum, Black Pepper, bornyl acetate, Cajeput, Camphor, Cedarwood, Cedarleaf oil, Chamomile, chlorbutanol, Cinnamon, Clary Sage Rosewood, Clove, *Eucalyptus*, Frankincense, *Geranium*, Ginger, Lavender, Lemon, Lemon essential oils, levomenthol, Lime, Menthol, Mint, Myrrh, nutmeg oil Orange, Patchouli, Peppermint, Pine Needle, Rose *Eucalyptus*, rosemary, Rosewood, Sage, Sandalwood, Spearmint, Tea Tree, terpinol, turpentine oil, thymol, Ylang Ylang or any combination thereof.

It is another object of the present invention to disclose the device as define above, wherein the drugs comprise in vaporized form at least one of the group of Braochodilators, especially sympatic mimetics, alfa antagonists, anti cholinergics; nasal decongestants, such as pseudoehedrines, ephedrines; steroids; anti histamines; anti prostaglandins, alternative or homeopathic medicaments; vaso constrictors; local anesthetics; mast cell stabilizers; antibiotics, such as biocides, fungicides etc; pleasant odor; pheromones; hormone treatments, such as ADH, insulin, growth hormones; vapors, humidifiers; drying compositions; hot or cold vapors; hyper-, iso- or hypotonic vapors or any combination thereof.

It is another object of the present invention to disclose the device as define above, wherein the drugs comprise in vaporized form at least one of the group of compositions and commercial available medicaments, their derivatives, or by-products provided thereof, selected from the group consisting of: Acrivastine, Aller-Eze Clemastine, Aller-Eze nasal spray, Azatadine maleate, Azelastine nasal spray, Beclometasone nasal spray, Beclometasone nasal spray, Beconase hayfever nasal spray, Beconase hayfever relief for adults, Beconase nasal spray, Benadryl allergy relief, Benadryl, Benadryl, Benadryl plus, Brompheniramine maleate, Budesonide nasal spray, Calimal Antihistamine, Cetirizine, Chlorphenamine, Clarityn, Clemastine, Cyproheptadine hydrochloride, Desloratadine, Dexa-Rhinaspray Duo. Dimotane elixir, Dimotane plus, Dimotapp elixir, Dimotapp elixir paediatric. Dimotapp LA, Flixonase allergy nasal spray, Flixonase aqueous nasal spray, Fluticasone propionate nasal spray, Galpharm hayfever and allergy relief, Galpseud Plus, Haymine, Histafen, Ipratropium bromide nasal spray, Levocabastine nasal spray, Levocetirizine dihydrochloride, Livostin direct nasal spray, Livostin nasal spray, Loratadine, Medised, Medised, Mistamine, Mizolastine, Mizollen, Mometasone furoate nasal spray, Nasacort, Nasobec nasal spray, Nasonex nasal spray, Neoclarityn tablets/syrup, Optimine syrup, Periactin, Phenergan, Piriteze, Piriton, Pollenase hayfever nasal spray, Promethazine hydrochloride elixir, Promethazine hydrochloride, Rhinocort Aqua, Rhinolast allergy nasal spray, Rhinolast nasal spray, Rinatec nasal spray, Rino clenil nasal spray, Rynacrom allergy nasal spray, Rynacrom nasal spray, Semprex, Sodium cromoglicate nasal spray, Sudafed Plus, Syntaris nasal spray, Tavegil, Telfast 120, Terfenadine, Terfinax, Triamcinolone acetonide, Vista-Methasone, Xyzal tablets, Zirtek allergy relief tablets, Zirtek allergy tablets/solution, Afrazine, Anadin, Beechams all-in-one, Beechams products, Benylin products, Contac, Day Nurse, Dimotapp elixir, Dimotapp elixir paediatric, Dimotapp products, Galpseud, Karvol decongestant products, Lemsip products, Meggezones, Merocets Plus lozenges, Nurofen Cold and Flu, Otrivine Menthol Nasal Spray, Otrivine Metered Dose Sinusitis Spray, Otrivine products, Pseudoephedrine hydrochloride, Sterwin real lemon cold powders and other products, Strepsils Menthol and *Eucalyptus* and other products, Sudafed and its products, Xylometazoline nasal drops, Bactroban Nasal, Fusafungine, Locabiotal, Naseptin nasal cream, Ipratropium bromide nasal spray, Rinatec nasal spray, pseudoephedrine, propylhexedrine, L-Desoxyephedrine, xylometazoline hydrochloride or any combination thereof.

It is another object of the present invention to disclose the device as define above, further comprising means for cooling or heating the fluid prior to or during or forcing the stream of fluid towards the respiratory tract.

It is another object of the present invention to disclose the device as define above, further comprising means for mixing or activating a medicament by reacting it with one or more reactants prior to or during dispensing of the drug.

It is another object of the present invention to disclose the device as define above, additionally comprising means for forcing the stream of fluid towards the respiratory tracts.

It is another object of the present invention to disclose the device as define above, comprising additional means of inhaling a dispersed medicament.

It is another object of the present invention to disclose the device as define above, wherein any part of the device is disposable.

It is another object of the present invention to disclose the device as define above, wherein said drug releasing mechanism is adapted to control the release of at least one drug from a combination of said containers.

It is another object of the present invention to disclose the device as define above, wherein any part of the device is reusable.

It is another object of the present invention to disclose the device as define above, wherein said pressure pulses are provided according to the treatment protocol of tables 1, 2, or 3.

It is another object of the present invention to disclose the device as define above, wherein said pressure pulses are provided according to a treatment protocol which is adapted to increase the uptake of medications.

It is another object of the present invention to disclose the device as define above, wherein said pressure pulses are provided according to a treatment protocol which is adapted to improve the clinical outcome of the treatment.

It is another object of the present invention to disclose a method for efficiently delivering drugs/medicaments to the respiratory system. The method comprising steps of:
a. Obtaining a device useful for facilitating delivery of drugs to the respiratory system of a user, the device comprising a mechanism for interrupting the airflow during inhalation or exhalation performed by the user through the device by generating pressure pulses within the respiratory system of the user, such that the delivery of the drugs to the user is facilitated; the pressure pulses are selected from the group consisting of: inspiratory Negative Pressure (NP) pulses, inspiratory Positive Pressure (PP) pulses, expiratory Negative Pressure (NP) pulses, expiratory Positive Pressure (PP) pulses into the respiratory system, and any combination thereof; and
b. operating the device, thereby facilitating the delivery of the drugs to the respiratory system.

It is another object of the present invention to disclose the method as define above, wherein the device is adapted for delivering the drugs to the upper respiratory tract of the respiratory system.

It is another object of the present invention to disclose the method as define above, wherein the device is adapted for delivering drugs to the lower respiratory tract of the respiratory system.

It is another object of the present invention to disclose a method for delivering drugs. The method comprises steps of:
a. providing a device useful for delivering drugs to the respiratory system of a user, the device comprising: (i) an air controlling mechanism for controlling passage of air during inhalation or exhalation of the air; (ii) at least one container for storing the drugs; and (iii) a drug releasing mechanism for delivering the drugs from the container to the user;
b. operating the device, thereby facilitating the delivery of the drugs to the respiratory system.

It is within the scope of the present invention that the air controlling mechanism is adapted to generate pressure pulses of Negative Pressure and/or Positive Pressure into the respiratory system during inspiration and/or expiration, and the drug releasing mechanism is adapted for entraining the drugs into the pressure pulses, such that uptake of the drugs by the tissues of the respiratory system is facilitated; the pressure pulses are selected from the group consisting of: inspiratory Negative Pressure (NP) pulses, inspiratory Positive Pressure (PP) pulses, expiratory Negative Pressure (NP) pulses, expiratory Positive Pressure (PP) pulses into the respiratory system, and any combination thereof.

It is another object of the present invention to disclose the method as define above, wherein the air controlling mechanism comprises means for forcing a stream of fluid towards the patient's respiratory system.

It is another object of the present invention to disclose the method as define above, wherein the device is adapted for delivery of powdered drug supplied in capsule form.

It is another object of the present invention to disclose the method as define above, wherein the air controlling mechanism comprises a shutter for interrupting the stream of air during patient's inspiration or expiration, such that a pulse of Negative Pressure is induced within the patient's respiratory system.

It is another object of the present invention to disclose the method as define above, wherein the shutter comprises a perforated rotating disc adapted to allow passage of the air through the perforation within the disc and to block and unblock the passage of the air.

It is another object of the present invention to disclose the method as define above, wherein the air controlling mechanism comprises a motor driven disc wheel adapted for synchronization with the drug releasing mechanism.

It is another object of the present invention to disclose the method as define above, wherein the drug releasing mechanism is adapted to be opened by a drop in pressure during inhalation and closed by a rise in pressure during exhalation.

It is another object of the present invention to disclose the method as define above, wherein the drug releasing mechanism comprises a drug releasing shutter for controlling release of the drugs from the container during the operation of the air controlling mechanism.

It is another object of the present invention to disclose the method as define above, wherein the device additionally comprises fluid vibrating means 26 (FVM) for vibrating the medication and the air to facilitate drug delivery, the FVM selected from the group comprising an acoustic means mechanical means or electromechanical (piezoelectric) means.

It is another object of the present invention to disclose the method as define above, wherein the FVM is located in the middle section of the device or proximally to the outlet of the container.

It is another object of the present invention to disclose the method as define above, wherein the container comprises a pressure generator for generating high pressure therein.

It is another object of the present invention to disclose the method as define above, wherein the device is pocket sized device.

It is another object of the present invention to disclose the method as define above, wherein the device is characterized by a non-drug mode in which the drug releasing mechanism does not provide drugs, and solely controls the passage of air during inhalation or exhalation of the air.

It is another object of the present invention to disclose the method as define above, wherein the device is adapted for use a s a sinusitis inhaler for use with one or both nostrils.

It is another object of the present invention to disclose the method as define above, further comprising a ratchet and pawl mechanism adapted to activate the device by lifting a pawl by the user's teeth.

It is another object of the present invention to disclose the method as define above, further comprising spirometric, chemical or other types of sensors adapted to measure parameters of the user's breath and to modify the treatment protocols of the device via a feedback mechanism, said sensors are adapted to measure parameters selected from the group consisting of: peak flow, flow rate, FEV 1, spirometric parameters, inhalation pressure, exhalation pressure, inspiratory pressure, expiratory pressure, vital capacity, inhaled $CO_2$ concentration, exhaled $CO_2$ concentration, inhaled $O_2$ concentration, exhaled $O_2$ concentration, and any combination thereof.

It is another object of the present invention to disclose the method as define above, wherein the device additionally comprises means for pulling the lower jaw forward with respect to the upper jaw such that the geometry of the upper airway facilitates smooth flow of air and drug into the lungs.

It is another object of the present invention to disclose the method as define above, wherein the drugs are selected from the group consisting of: vaporized essential oils, volatile compounds, etheric oils, terepenes, terpanols and either water miscible or water-immiscible extracts, especially oils or extracts obtained from *Amyris*, Balsam, Bay Rum, Black Pepper, bornyl acetate, Cajeput, Camphor, Cedarwood, Cedarleaf oil, Chamomile, chlorbutanol, Cinnamon, Clary Sage Rosewood, Clove, *Eucalyptus*, Frankincense, *Geranium*, Ginger, Lavender, Lemon, Lemon essential oils, levomenthol, Lime, Menthol, Mint, Myrrh, nutmeg oil Orange, Patchouli, Peppermint, Pine Needle, Rose *Eucalyptus*, rosemary, Rosewood, Sage, Sandalwood, Spearmint, Tea Tree, terpinol, turpentine oil, thymol, Ylang Ylang or any combination thereof.

It is another object of the present invention to disclose the method as define above, wherein the drugs comprise in vaporized form at least one of the group of Braochodilators, especially sympatic mimetics, alfa antagonists, anti cholinergics; nasal decongestants, such as pseudoehedrines, ephedrines; steroids; anti histamines; anti prostaglandins, alternative or homeopathic medicaments; vaso constrictors; local anesthetics; mast cell stabilizers; antibiotics, such as biocides, fungicides etc; pleasant odor; pheromones; hormone treatments, such as ADH, insulin, growth hormones; vapors, humidifiers; drying compositions; hot or cold vapors; hyper-, iso- or hypotonic vapors or any combination thereof.

It is another object of the present invention to disclose the method as define above, wherein the drugs comprise in vaporized form at least one of the group of compositions and commercial available medicaments, their derivatives, or by-products provided thereof, selected from the group consisting of: Acrivastine, Aller-Eze Clemastine, Aller-Eze nasal spray, Azatadine maleate, Azelastine nasal spray, Beclometasone nasal spray, Beclometasone nasal spray, Beconase hayfever nasal spray, Beconase hayfever relief for adults, Beconase nasal spray, Benadryl allergy relief, Benadryl, Benadryl, Benadryl plus, Brompheniramine maleate, Budesonide nasal spray, Calimal Antihistamine, Cetirizine, Chlorphenamine, Clarityn, Clemastine, Cyproheptadine hydrochloride, Desloratadine, Dexa-Rhinaspray Duo. Dimotane elixir, Dimotane plus, Dimotapp elixir, Dimotapp elixir paediatric. Dimotapp LA, Flixonase allergy nasal spray, Flixonase aqueous nasal spray, Fluticasone propionate nasal spray, Galpharm hayfever and allergy relief, Galpseud Plus, Haymine, Histafen, Ipratropium bromide nasal spray, Levocabastine nasal spray, Levocetirizine dihydrochloride, Livostin direct nasal spray, Livostin nasal spray, Loratadine, Medised, Medised, Mistamine, Mizolastine, Mizollen, Mometasone furoate nasal spray, Nasacort, Nasobec nasal spray, Nasonex nasal spray, Neoclarityn tablets/syrup, Optimine syrup, Periactin, Phenergan, Piriteze, Piriton, Pollenase hayfever nasal spray, Promethazine hydrochloride elixir, Promethazine hydrochloride, Rhinocort Aqua, Rhinolast allergy nasal spray, Rhinolast nasal spray, Rinatec nasal spray, Rino clenil nasal spray, Rynacrom allergy nasal spray, Rynacrom nasal spray, Semprex, Sodium cromoglicate nasal spray, Sudafed Plus, Syntaris nasal spray, Tavegil, Telfast 120, Terfenadine, Terfinax, Triamcinolone acetonide, Vista-Methasone, Xyzal tablets, Zirtek allergy relief tablets, Zirtek allergy tablets/solution, Afrazine, Anadin, Beechams all-in-one, Beechams products, Benylin products, Contac, Day Nurse, Dimotapp elixir, Dimotapp elixir paediatric, Dimotapp products, Galpseud, Karvol decongestant products, Lemsip products, Meggezones, Merocets Plus lozenges, Nurofen Cold and Flu, Otrivine Menthol Nasal Spray, Otrivine Metered Dose Sinusitis Spray, Otrivine products, Pseudoephedrine hydrochloride, Sterwin real lemon cold powders and other products, Strepsils Menthol and *Eucalyptus* and other products, Sudafed and its products, Xylometazoline nasal drops, Bactroban Nasal, Fusafungine, Locabiotal, Naseptin nasal cream, Ipratropium bromide nasal spray, Rinatec nasal spray, pseudoephedrine, propylhexedrine, L-Desoxyephedrine, xylometazoline hydrochloride or any combination thereof.

It is another object of the present invention to disclose the method as define above, further comprising means for cooling or heating the fluid prior to or during or forcing the stream of fluid towards the respiratory tract.

It is another object of the present invention to disclose the method as define above, further comprising means for mixing or activating a medicament by reacting it with one or more reactants prior to or during dispensing of the drug.

It is another object of the present invention to disclose the method as define above, additionally comprising means for forcing the stream of fluid towards the respiratory tracts.

It is another object of the present invention to disclose the method as define above, comprising additional means of inhaling a dispersed medicament.

It is another object of the present invention to disclose the method as define above, wherein any part of the device is disposable.

It is another object of the present invention to disclose the method as define above, wherein any part of the device is reusable.

It is another object of the present invention to disclose the method as define above, wherein said drug releasing mechanism is adapted to control the release of at least one drug from a combination of said containers.

It is another object of the present invention to disclose the method as define above, wherein said pressure pulses are provided according to the treatment protocol of tables 1, 2, or 3.

It is another object of the present invention to disclose the method as define above, wherein said pressure pulses are provided according to a treatment protocol which is adapted to increase the uptake of medications.

It is another object of the present invention to disclose the method as define above, wherein said pressure pulses are provided according to a treatment protocol which is adapted to improve the clinical outcome of the treatment.

DETAILED DESCRIPTION OF THE DRAWINGS

Figure 1A:
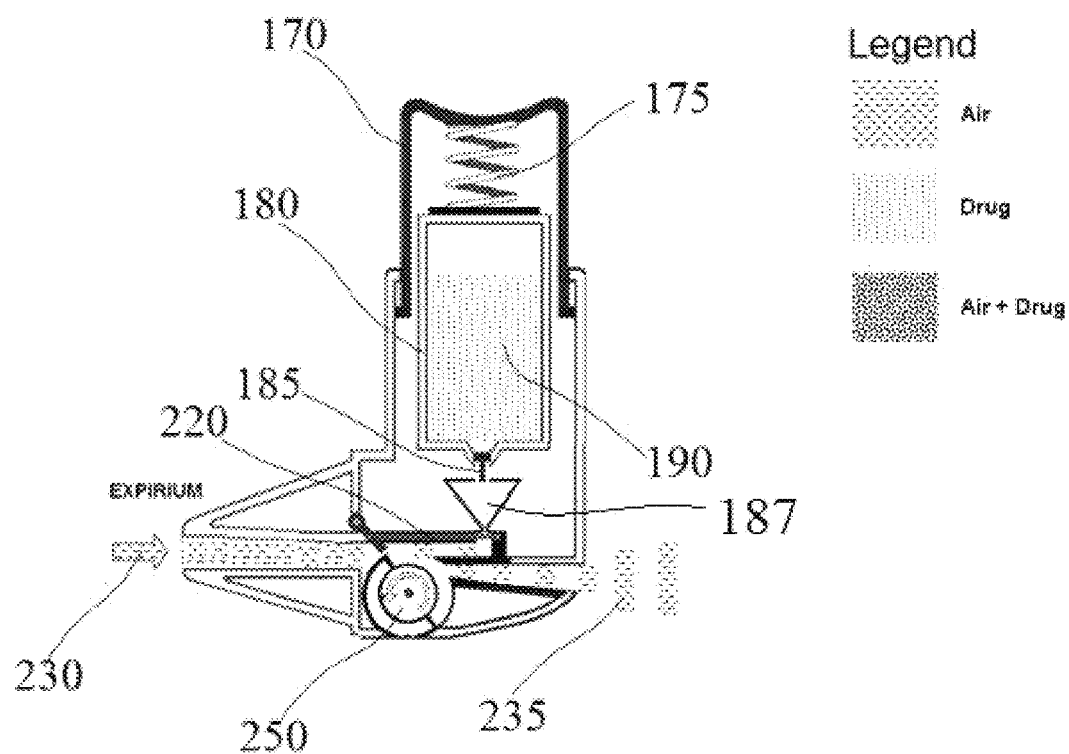
FIGS. 1*a* and 1*b* schematically illustrate an embodiment of the device at exhalation and inhalation phases, respectively.
Figure 1B:
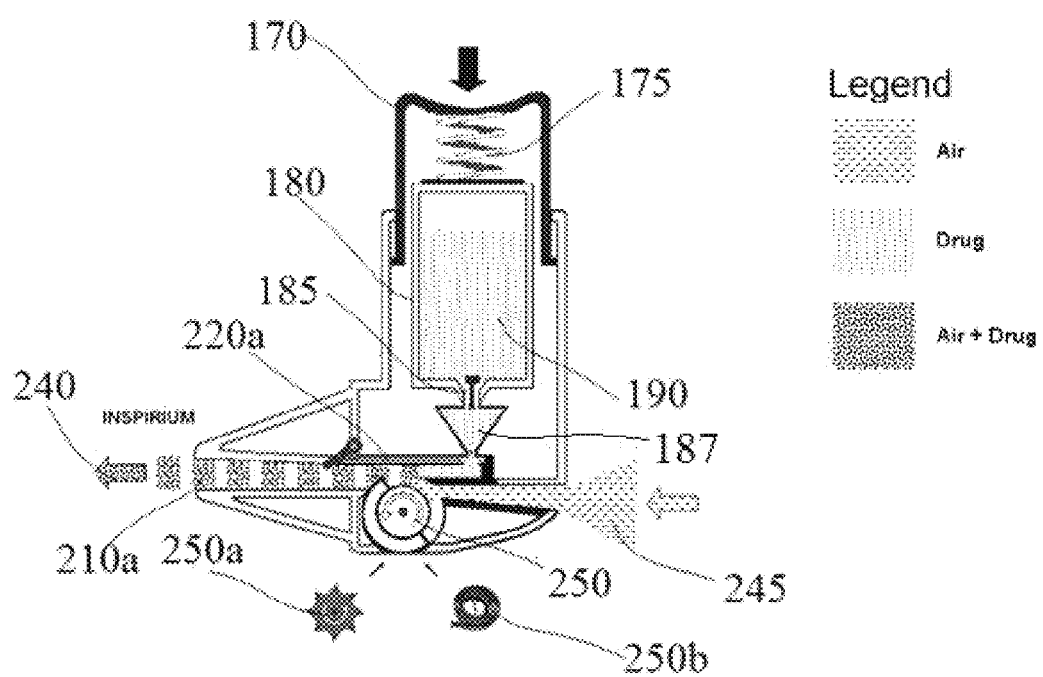
Figure 1C:
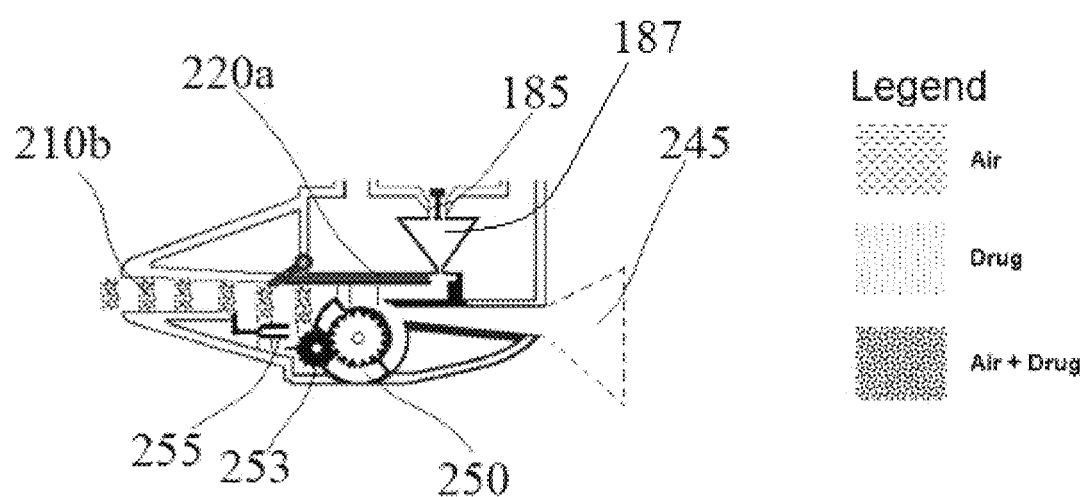
FIG. 1*c* schematically illustrates an embodiment of the device using a 'tuning fork' resonator for nebulization.

The core of the present invention is hereby illustrated by the following drawings and explanations.

The present invention is directed to providing devices and methods for improving drug delivery to the respiratory system, including the lower respiratory tract (the lungs) and the upper respiratory tract (nose, sinuses).

The term 'air' refers hereinafter to any type of gas which may be delivery to the lungs of a user during inhalation and/or exhalation. For example, the term 'air' may refer to a pure air, a gas, or a mixture of air/gas with a drug.

The term 'fluid' refers hereinafter to a mixture of a gas such as air and at least one liquid or gas other than air, or air itself, or any drug or medicament in any convenient form, especially nebulized, vaporized or powdered.

According to different embodiments of the present invention, the terms 'air' and 'fluid' may refers to same substance.

The term 'drugs' refers hereinafter to any kind of at least one substance or medicament which may be supplied to the human respiratory system.

The term 'inspiratory Negative Pressure' refers to creation of Negative Pressure during inspiration, for example by closing the passage of air through the device, and then opening the passage. Negative pressure can also be reached by drawing (sucking) air pulse from the respiratory system during inspiration.

The term 'inspiratory Positive Pressure' refers to creation of Positive Pressure during inspiration, for example by adding pulses of air to the lungs during inspiration.

The term 'expiratory Positive Pressure' refers to creation of Positive Pressure during expiration, for example by adding (delivering) pulses of air to the lungs during expiration.

FIGS. 2a-d shows schematically the effects of pulsating high negative pressure (Vacuum) pulses on the airways and subsequently on the respiratory system.

The term 'expiratory Negative Pressure' refers to creation of Negative Pressure during expiration, for example by drawing (sucking) pulses of air from the mouth during expiration A patient exhales air in normal breathing, creating positive pressure in the lungs and chest cavity. Then inhalation begins, in which a Normal Negative Pressure (NNP) is created in the lungs and chest cavity. However if, whilst the patient is inspiring air, the patient blocks his airway with the tongue or the soft palate, an immediate high negative pressure will be felt in the chest cavity. This is due to expansion of the chest cavity by the diaphragm and other chest cavity muscles: air has been expelled (expiration), after which the chest wall expands to draw in more air. If no more air can enter (i.e. if the tongue and the soft palate has now blocked or stopped the air passage) then a situation of high negative pressure obtains in the lungs and chest cavity. It is clear that this can be done repeatedly, for example by blocking and unblocking air passages, thus creating a series of High Negative Pressure (HNP) pulses over the NNP in the lungs. In the present invention, devices and methods are presented for producing HNP pulses as a method of facilitating drug delivery to the airways and lungs, and/or to aid in certain conditions requiring mucous dislodgement, etc. The method works by inducing the HNP pulses by means of a device specially designed for the purpose, which also delivers drugs via nebulization or any other convenient means. Thus, vacuum pulses are produced whilst drug delivery is provided.

As will be obvious to one skilled in the art, the air flow coming from the user upon exhalation can also be intermittently blocked in similar fashion, providing a series of high positive pressure (HPP) pulses.

According to different embodiments of the present invention, the terms 'High Negative Pressure' and 'Negative Pressure' have the same meaning. Moreover, according to different embodiments of the present invention, the terms 'High Positive Pressure' and 'Positive Pressure' have the same meaning.

According to one embodiment of the present invention the system forces a stream of fluid towards the patient's respiratory tracts. The term 'forcing' refers hereinafter to the generation of flowing fluid either as a continuous flow or as pulses by means of vents, fans, jets, injectors, compressors, pumping means or other means known in the art adapted to force a fluid towards at least one predetermined location such as the lungs.

The present invention discloses a device useful for facilitating delivery of drugs to the respiratory system of a user. The device comprises a mechanism for interrupting the airflow during inhalation or exhalation performed by the user through the device by generating pressure pulses within the respiratory system of the user, such that the delivery of the drugs to the user is facilitated. The pressure pulses may be selected from the group consisting of: inspiratory Negative Pressure (NP) pulses, inspiratory Positive Pressure (PP) pulses, expiratory Negative Pressure (NP) pulses, expiratory Positive Pressure (PP) pulses into said respiratory system, and any combination thereof.

According to some embodiments, the device may deliver the drugs to the upper respiratory tract of the respiratory system. According to other embodiments, the device may deliver drugs to the lower respiratory tract of the respiratory system.

According to different embodiments of the present invention, the present invention discloses a device useful for delivering drugs to the respiratory system of a user. The device comprises:
a. an air controlling mechanism for controlling passage of air during inhalation or exhalation of said air;
b. at least one container for storing said drugs;
c. a drug releasing mechanism for delivering said drugs from said container to said user;

The air controlling mechanism is adapted to generate pressure pulses of Negative Pressure and/or Positive Pressure into the respiratory system during inspiration and/or expiration, and the drug releasing mechanism is adapted for entraining the drugs into the pressure pulses, such that uptake of the drugs by the tissues of the respiratory system is facilitated. The pressure pulses may be selected from the group consisting of: inspiratory Negative Pressure (NP) pulses, inspiratory Positive Pressure (PP) pulses, expiratory Negative Pressure (NP) pulses, expiratory Positive Pressure (PP) pulses into said respiratory system, and any combination thereof.

In one embodiment of the invention a device is employed for introducing air and medicaments during inspiration (whilst the patient breathes in). The device has a shutter mechanism which opens and closes in a predetermined manner. When the shutter is open, air may enter the airways, and the normal negative pressure (NNP) is experienced by the airways. When the shutter closes, the aforementioned HNP is produced in the airways due to continued chest cavity expansion with a lack of fluid intake. This can be explained by the Boyle-Mariotte law according to which $p_1 V_1 = p_2 V_2$.

This has a mechanical effect of narrowing the airways, and when the shutter is reopened, a 'rebound effect' takes place. The rebound effect, which comprises a series of pressure waves passing through tissue, is described by Avni in U.S. patent application 61/250,528, and this document is herein incorporated by reference in its entirety. Said tissue rebound will have profound effects on facilitation of blood supply, oxygenation, perfusion, CO2 and NO production and other physiologically important functions of cells and tissues. In addition, and possibly as a consequence of the aforementioned, drugs which are introduced in the airstream penetrate the lungs further towards the terminal bronchioles and alveoli; and also, the drug particles impinge and impact on the tissue walls, and increased rates and efficiency of drug uptake is achieved.

Figure 2A:
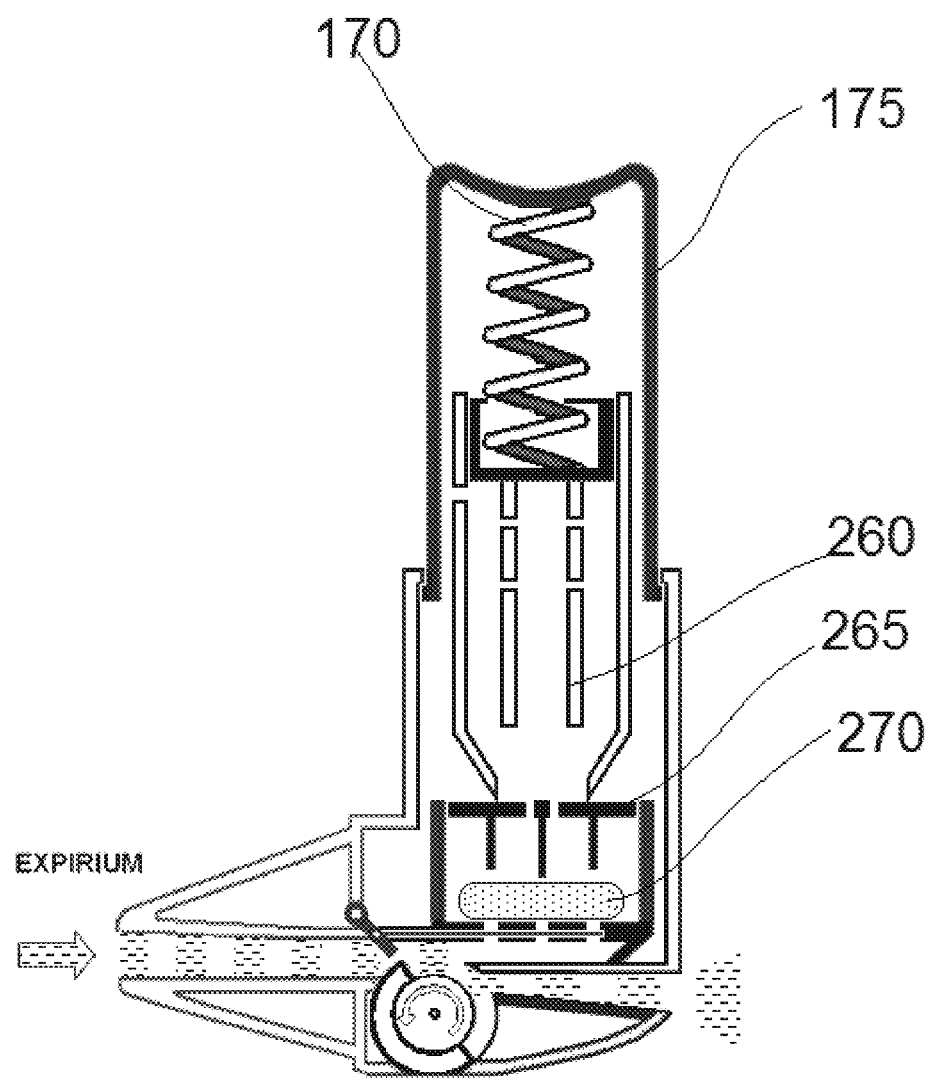
FIGS. 2*a* and 2*b* schematically illustrate an embodiment of the invention using a drug capsule at exhalation and inhalation phases, respectively.

FIGS. 2a to 2e present another embodiment of the present invention provided with wheel 250 intermittently blocking a flow of exhaled/inhaled air 230/240. As a result, pressure pulses 210a/210b/235 are generated. The wheel can be driven by and electric motor (not shown). The device comprises container 180 accommodating medicine 190. The aforesaid medicine is released by button 170 via spring 175. Container 180 is brought down such that valve 185 opens. As seen in FIG. 2a corresponding to the exhalation phase, exhaled air 235 forces medicine shutter to be in a closed position 220 and a medicine dose released from container 180 is coned up within a secondary chamber 187. At the inhalation phase (see FIG. 2b), inhaled air 240 brings the medicine shutter into an open position 220a and the medicine dose accommodated within secondary chamber 187 is dispensed into inhaled air 240. In this case, a dispensed dose of the medicine is mixed with the inhaled air and pressure pulses 210a/210b conveyed into patient's lungs contain the dispensed dose of the medicine. The aerosolized or atomized medicament stream is forcibly ejected from the device due to its pressure, which in general will be greater than the ambient pressure. The fluid vibrating means (FVM) may comprise an acoustic resonator, a piezoelectric element, or other vibrating mechanism as will be known to one skilled in the art. In yet another embodiment, an acoustic or mechanical element or electromechanical (piezoelectric) element vibrates the medication and the air to facilitate drug delivery. This element could for example be located in the middle of the airstream or near the outlet of the drug container. In FIG. 2c, tuning fork 255 actuated by cogwheel 253 engaged with the wheel 250.

The device also comprises a drug releasing mechanism 28 adapted to control the passage of the drugs from the container.

According to some embodiments, by means of rotation of a cogwheel, a shutter may be alternately opened and closed thus provided alternate NNP and HNP pulses. Following this, a slow release of the drug combines with HNP pulses may be provided. By this means the amount of drug delivered may be metered to an exact dose.

Figure 1D:
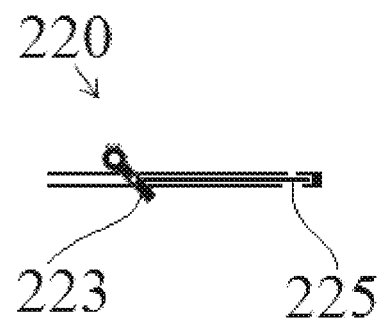
FIGS. 1*d* and 1*e* schematically illustrate medicine shutter in closed and opened positions, respectively.
Figure 1E:
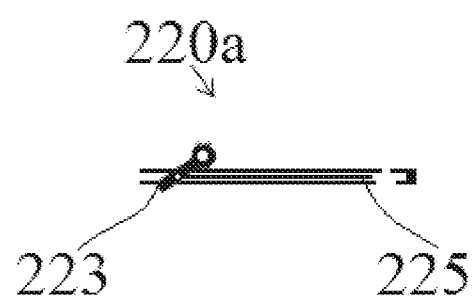

According to some embodiments, a dry powder drug capsule or container may also be used to administer the drug to the patient. A button is depressed by the user as in a standard inhaler. Meanwhile a rotating disc is activated that alternately blocks or opens a passage allowing or disallowing fluid flow out of the device. As the user inhales, alternating pulses of NNP and HNP are thereby administered, the NNP pulses allowing fluid flow and medicine delivery to the patient, and the HNP parts of the cycle increasing the negative pressure in the chest cavity and lungs. The next NNP pulse induces a rebound effect on the respiratory tissues due to the sudden inrush of fluid. FIGS. 1d and 1e illustrate an operating principle of medicine shutter. At the exhalation phase, element 223 having a sufficient area brings shuttering member 225 into the closed position, while at the exhalation phase, the shuttering member 225is brought into the open position.

Figure 2B:
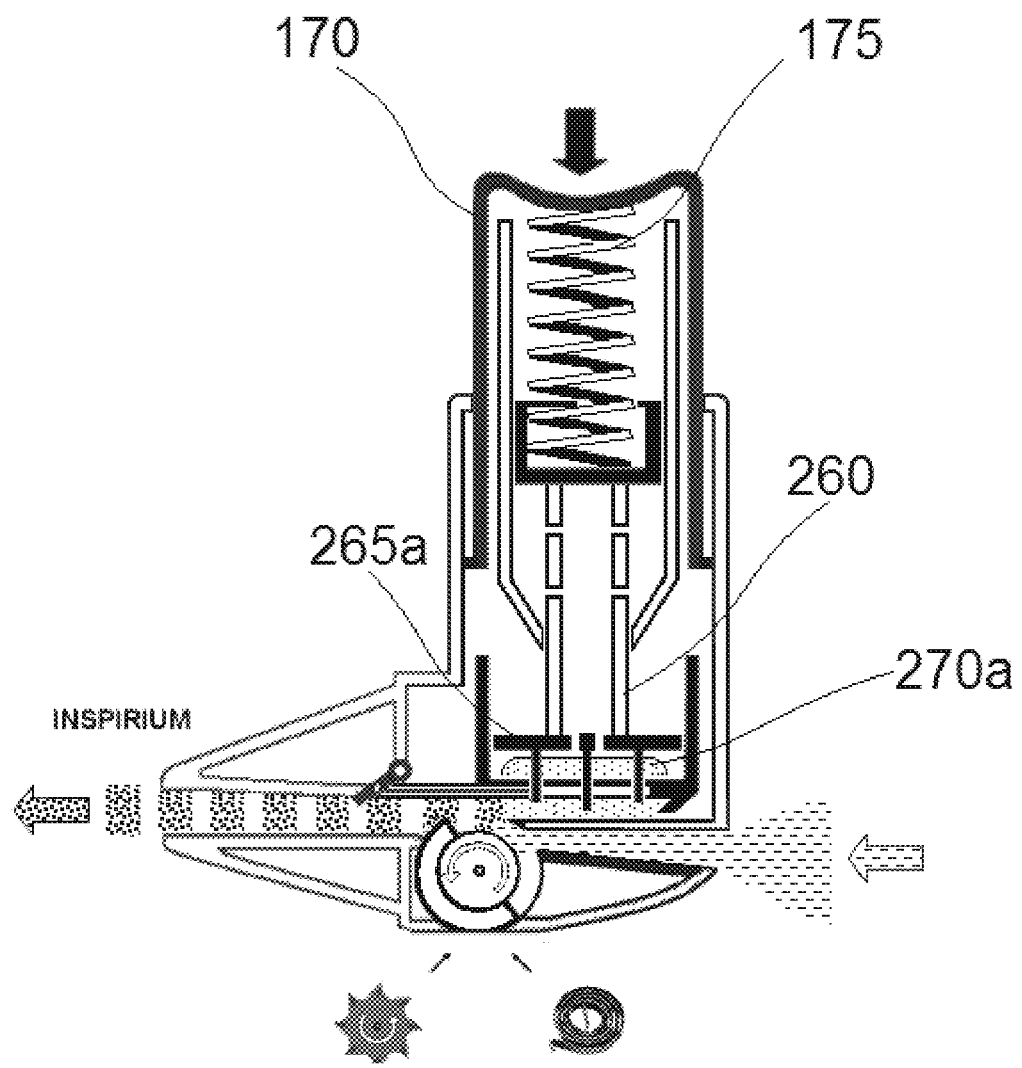

In FIGS. 2a and 2b an embodiment configured for dispensing medicine from capsule 270 is shown. Specifically, the button 170 via spring 175 and elongate member 260 forces piercing member 265 to dispense a medicine contained in capsule 270. Referring to FIG. 2a, the device is in a stand-by position and piercing element is in position 265 over capsule 270. In FIG. 2b, piercing element is in position 265a such that the contained medicine is dispensed from pierced capsule 270a.

In another embodiment of the device, the resistance of the device to the flow of the exhaled airstream can be controlled according to a predetermined program. This resistance control may be implemented by narrowing of the airstream conduit at the device's outlet in the mouthpiece, at the location of drug pickup by the airstream, at the device's air inlet or at any other location along the device's exhaled airstream path. This resistance control may also, or alternatively, be implemented by increasing resistance to rotation of the turbine while the latter is rotating due to the exhaled airstream. This turbine resistance control may be automatic, based on changes in air pressure or flow, or based on data provided by one or more sensors that monitor biological information such as gas levels in the exhaled air. The turbine resistance control may, alternatively, be manual, by setting of a shutter, valve or other mechanisms, or by replacing parts that affect flow resistance such as the mouthpiece.

According to some embodiment, the sensors of the present invention may be connected to a feedback mechanism which may modify the treatment protocols of the device via a feedback mechanism. The feedback mechanism may receive physiological or other data from the sensors, and operate the drug releasing mechanism or the air controlling mechanism accordingly.

In another embodiment of the device, the size and/or shape of the mouthpiece can be controlled, in order to affect the way the patient's lips are placed around the mouthpiece and/or the angle of the jaw and/or how large the mouth is opened when using the device. As an example, the mouthpiece can be designed with notches for the upper and lower teeth, in order to pull the lower jaw forward such that the geometry of the upper airway facilitates the smooth flow of the air and drug into the lungs. Control of the size and shape of the mouth is also important as it affects the chest cavity and airways resonance and acoustics, similar to the phenomenon known in singing and playing wind instruments, and improves drug dispersion in the lungs.

In another embodiment, there is an element in the device that vibrates and creates vibrational frequency(ies) in the inhaled or exhaled airstream.

It is within provision of the invention that as part of a protocol, the pressure introduced into the lungs be reduced and increased at a certain frequency, to create pulses of positive and negative pressure in the patient lungs.

The pressure necessary for operation of the device can be derived from a piston, turbine, spring, or other source as will be obvious to one skilled in the art. The present invention also discloses a special feature of the device intended to increase the effectiveness thereof. By means of special indentations on the mouthpiece of the device, the lower jaw is pulled forward. As will be known to one skilled in the art this tends to increase the diameter of the upper respiratory passages, and to align them thus facilitating greater flow and increased uptake of the medicament or other fluid provided by the inhaler.

It is one provision of the invention that the user's natural inspiration be intermittently blocked by means of blocking the incoming airflow, with a shutter or the like. By this means a series of repeating ambient and low pressures are introduced into the respiratory passages. It is also within provision of the invention that expiration be similarly blocked, producing a similar series of high positive and ambient pressures. As will be clear to one skilled in the art this will tend to release mucous blockages, increase uptake, and provide for better gas exchange.

Figure 3A:
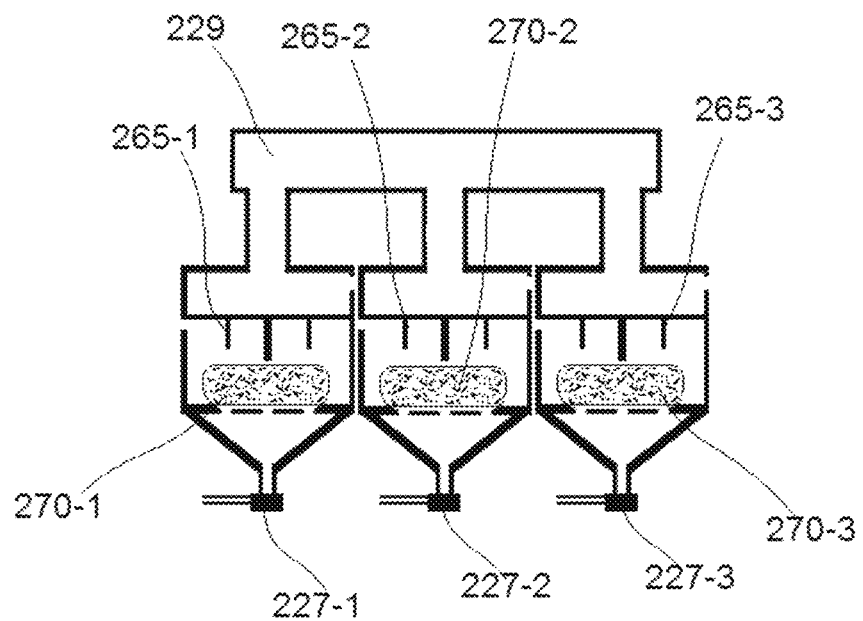
FIGS. 3*a* to 3*d* schematically illustrate the device of the present invention with three containers for storing drugs where all containers are closed (FIG. 3*a*), a central container is open (FIG. 3*b*); a left container is open (FIG. 3*c*); a right container is open (FIG. 3*d*).
Figure 3B:
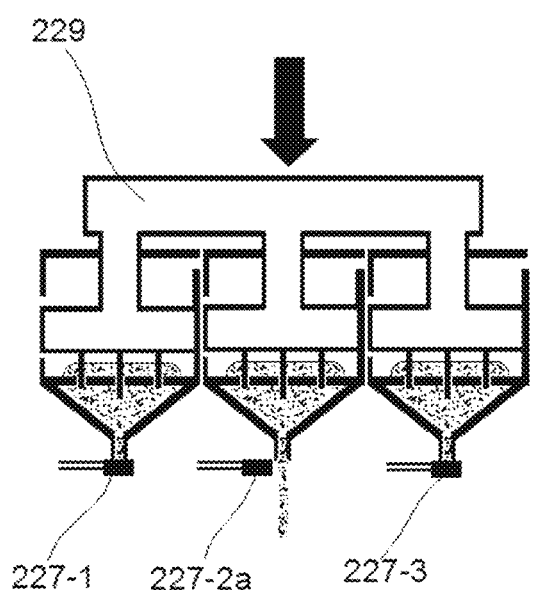
Figure 3C:
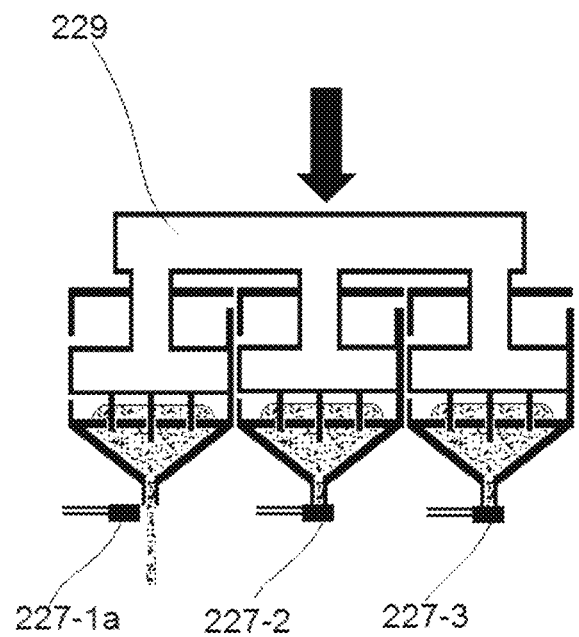
Figure 3D:
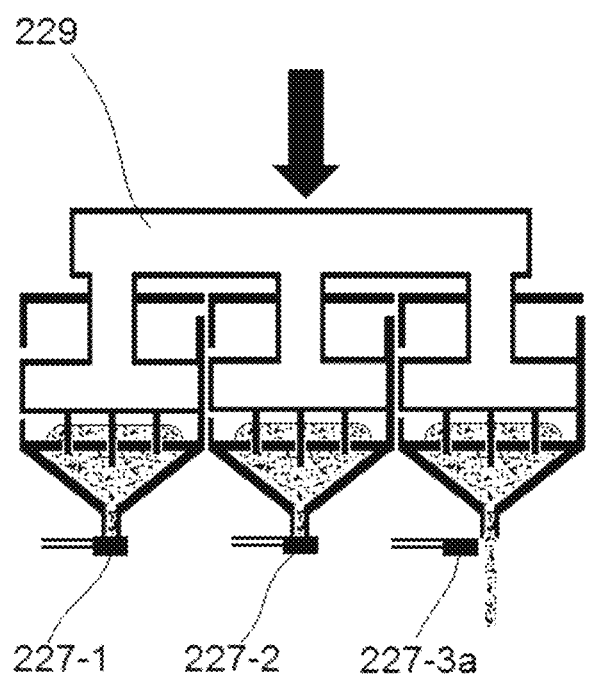

Reference is now made to FIGS. 3a to 3d which schematically illustrates another embodiment of the present invention. According to the embodiment in FIG. 3a, the container of the present invention may be a combination of containers 229. According to this embodiment, the drug releasing mechanism may control from which container of the combination of containers the drug will be released at a predetermined time and according to predetermined conditions. For example, the drug releasing mechanism may be controlled by a mechanical/electrical controller which may open or close a shutter 227-1/227-2/ 227-3 from which the drug may be released. After piercing capsules 270-1/270-2/ 270-3 by means of piercing members 265-1/265-2/265-3, the device is ready to dispense any medicine contained in capsules 270-1/270-2/270-3. FIGS. 3b to 3d successively show dispensing medicines contained in capsules 270-1/ 270-2/270-3. Moreover, the operation of the drug releasing mechanism may be performed according to the data received from the sensors (not shown) of the present invention, or according to a predefined timing of each container. These sensors may measure parameters selected from the group consisting of: peak flow, flow rate, FEV 1, spirometric parameters, inhalation pressure, exhalation pressure, inspiratory pressure, expiratory pressure, vital capacity, inhaled $CO_2$ concentration, exhaled $CO_2$ concentration, inhaled $O_2$ concentration, exhaled $O_2$ concentration, and any combination thereof.

Moreover, the drug releasing mechanism may be activated in a synchronization of predetermined treatment protocols, such that each drug is released according to the same treatment protocol, or according to different treatment protocols.

Figure 4A:
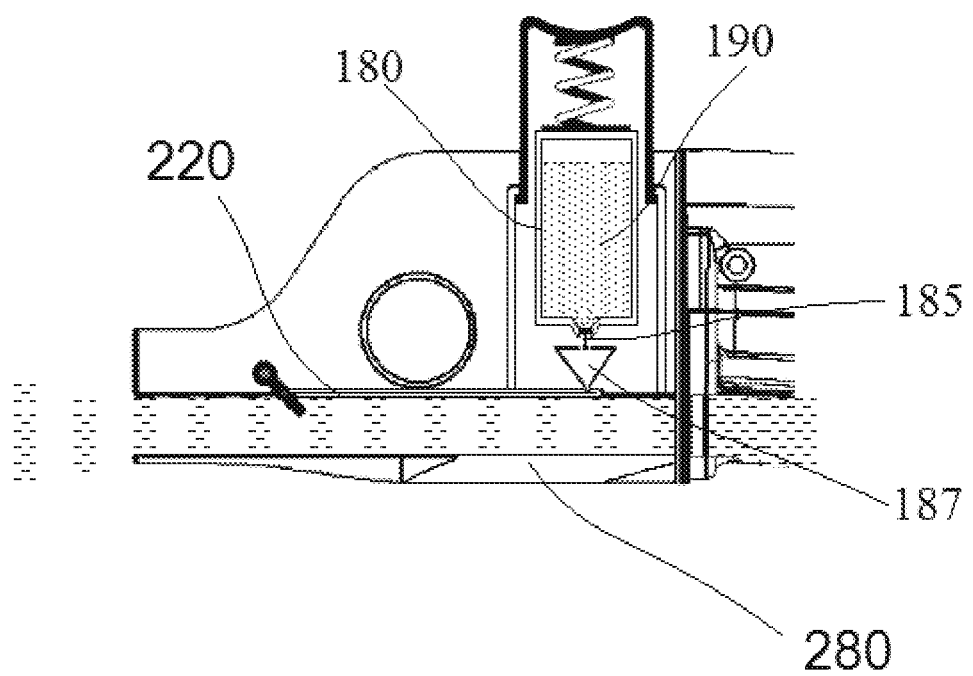
FIGS. 4*a* and 4*b* schematically illustrate a further embodiment of the device provided with an air controlling mechanism at exhalation and inhalation phases, respectively.
Figure 4B:
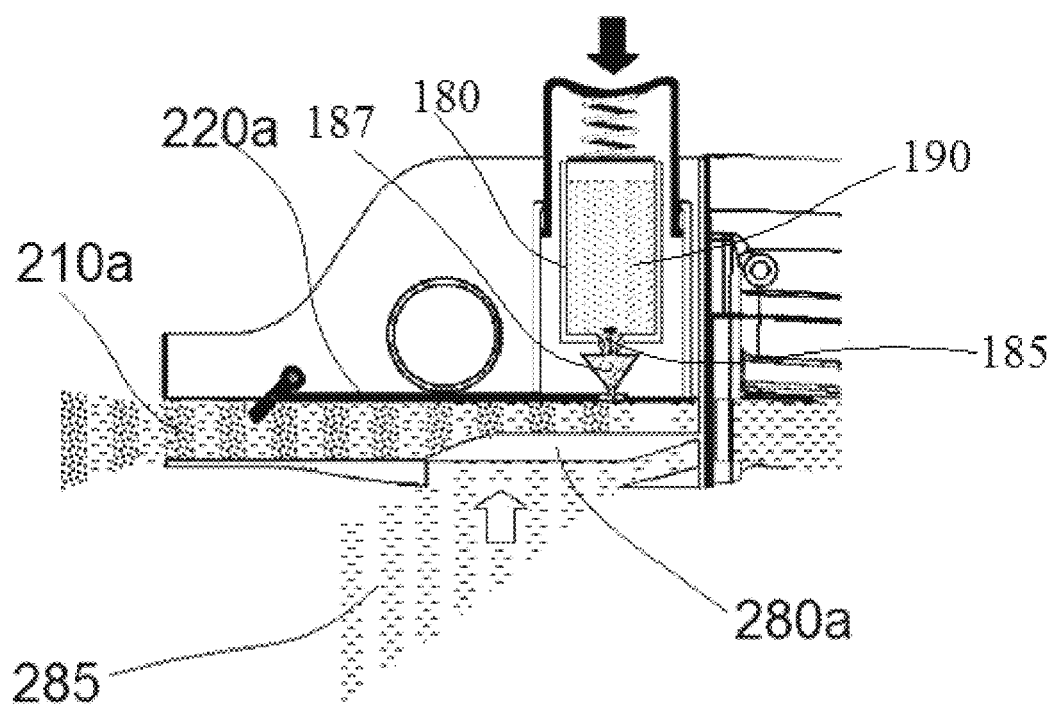

In FIGS. 4a and 4b, another embodiment of the invention is shown during expiration and inspiration, respectively. The bands indicate regions of alternating high and low pressure. The device of the present invention is able to produce series of positive and negative pressure pulses during expiration and inspiration. Air controlling mechanism 280 can be seen in two different positions. Air controlling mechanism 280 is closed during the expiration phase while at the inhalation phase the aforesaid air controlling mechanism provides a bypass to relieve breathing resistance.

Figure 4C:
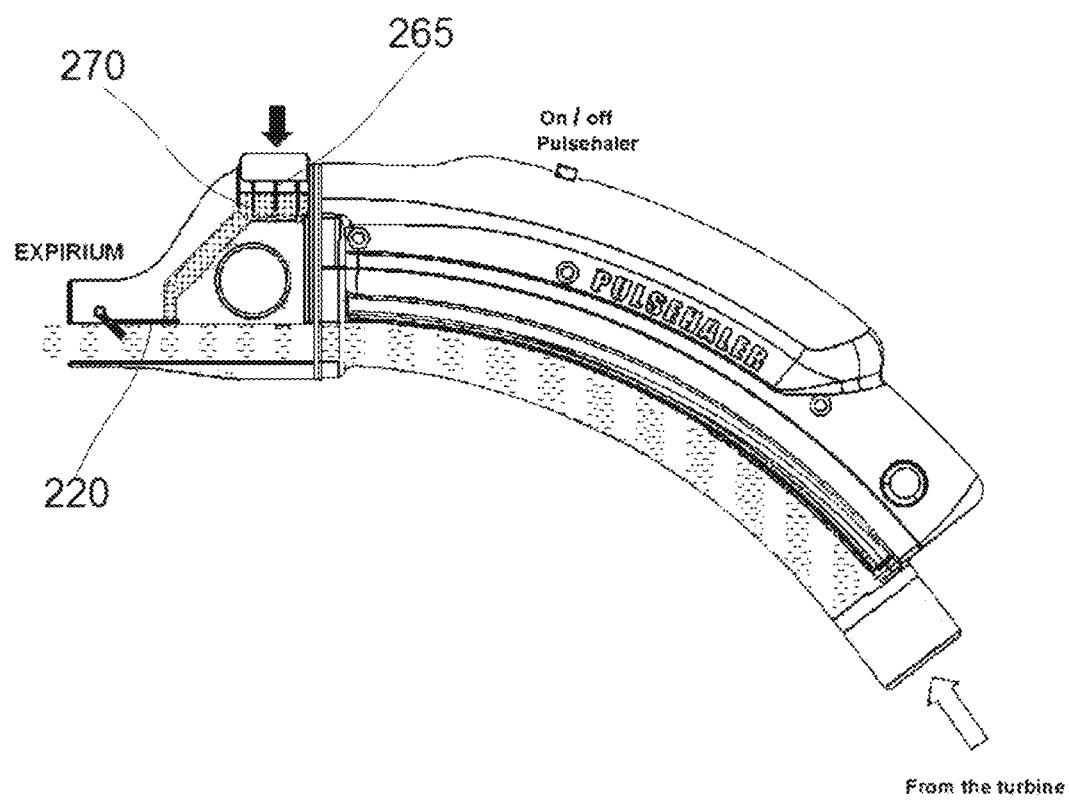
FIG. 4*c* schematically illustrates a further embodiment of the device provided with a drug door.

In FIG. 4c another embodiment of the invention is shown during expiration and inspiration. In this figure, a further embodiment of the device is shown, in which dry powder capsule 270 is used with a curved tube. Drug door 220 can be opened or closed, allowing or blocking powder from entering the fluid flow. This fluid flow is periodically interrupted by means of a wheel or shutter as will be clear to one skilled in the art.

Figure 5A:
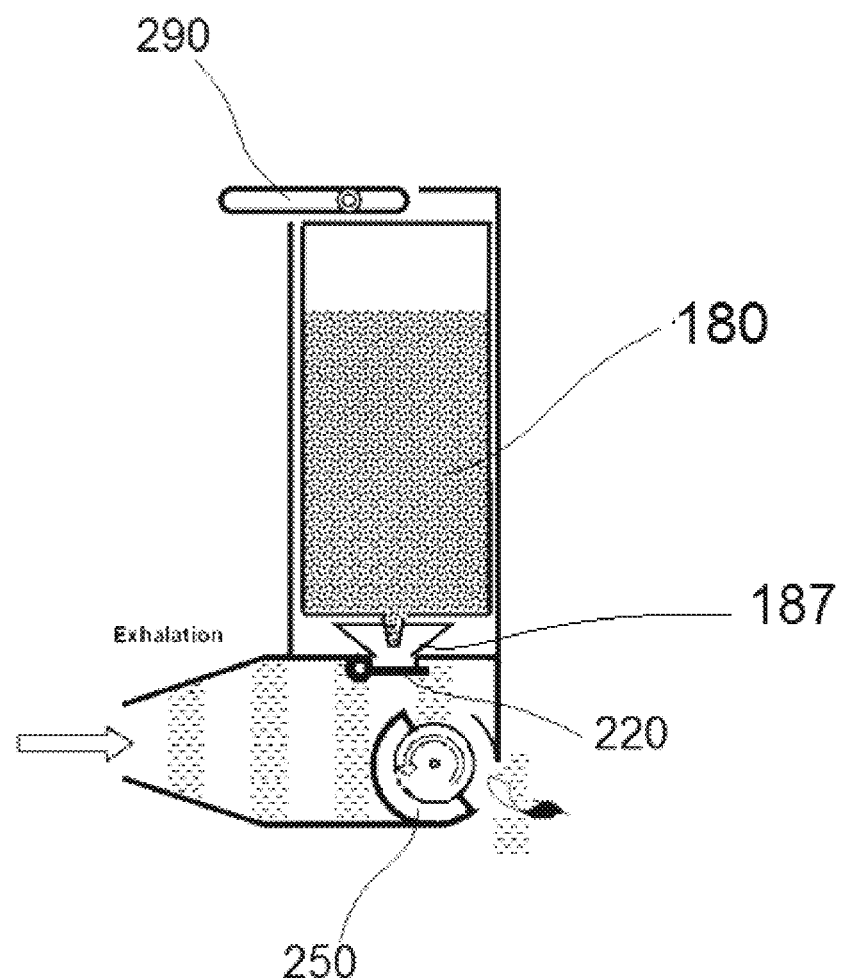
FIGS. 5a and 5b schematically illustrate a further embodiment of the device with a rotating disc which is employed to periodically block the inlet of fluid into the user's lungs at expiration and inspiration phases, respectively.
Figure 5B:
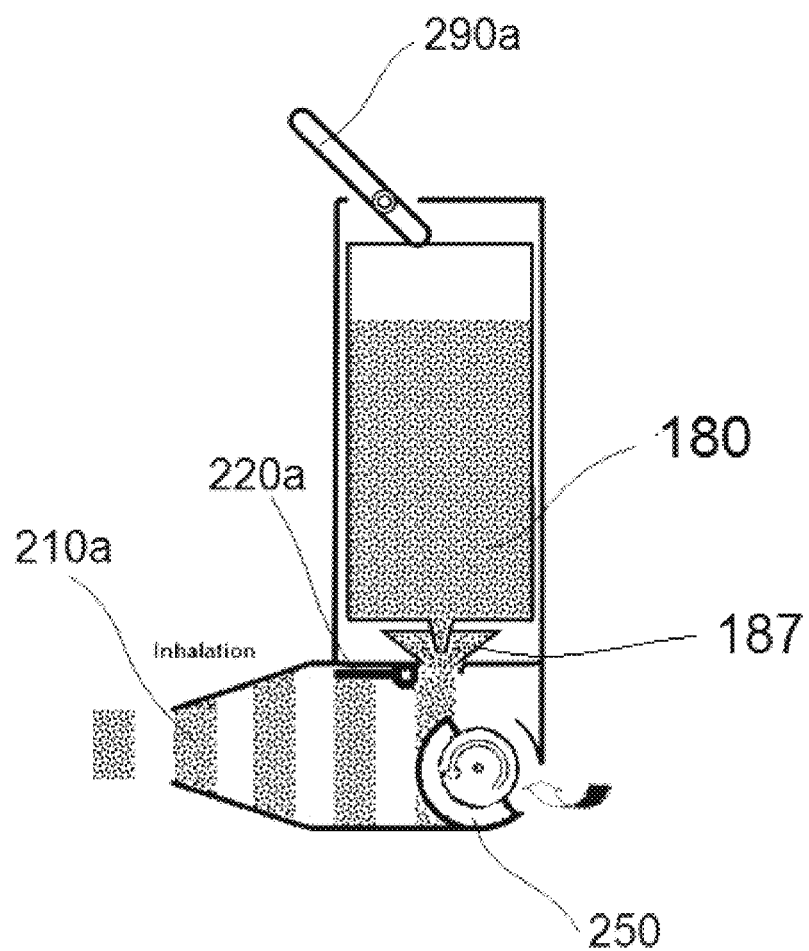
Figure 5C:
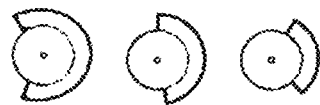
FIG. 5c schematically illustrates exemplar embodiments of the rotating disc.

Referring to FIGS. 5a and 5b, a rotating disc is employed to periodically block the inlet of fluid into the user's lungs. The 'duty cycle' or ratio of block to unblocked time can be varied by means of different discs 250, as shown. The container with medicine 190 is depressed by lever down to dispense medicine 190 into inhaled air through open shutter 220a. The generated pneumatic pulses 210a are provided into patient's lungs.

It is within provision of the device to provide a 'pocket inhaler' which may be useful with or without medication. Without medication, the device is used to introduce pressure fluctuations into the lungs, thereby vibrating and massaging the air passages, dislodging mucous, increasing perfusion and the like as will be obvious to one skilled in the art. The device may also be used for drug delivery, by means of introducing a medicament into the fluid stream that flows in pulses into the user's airways.

Figure 6A:
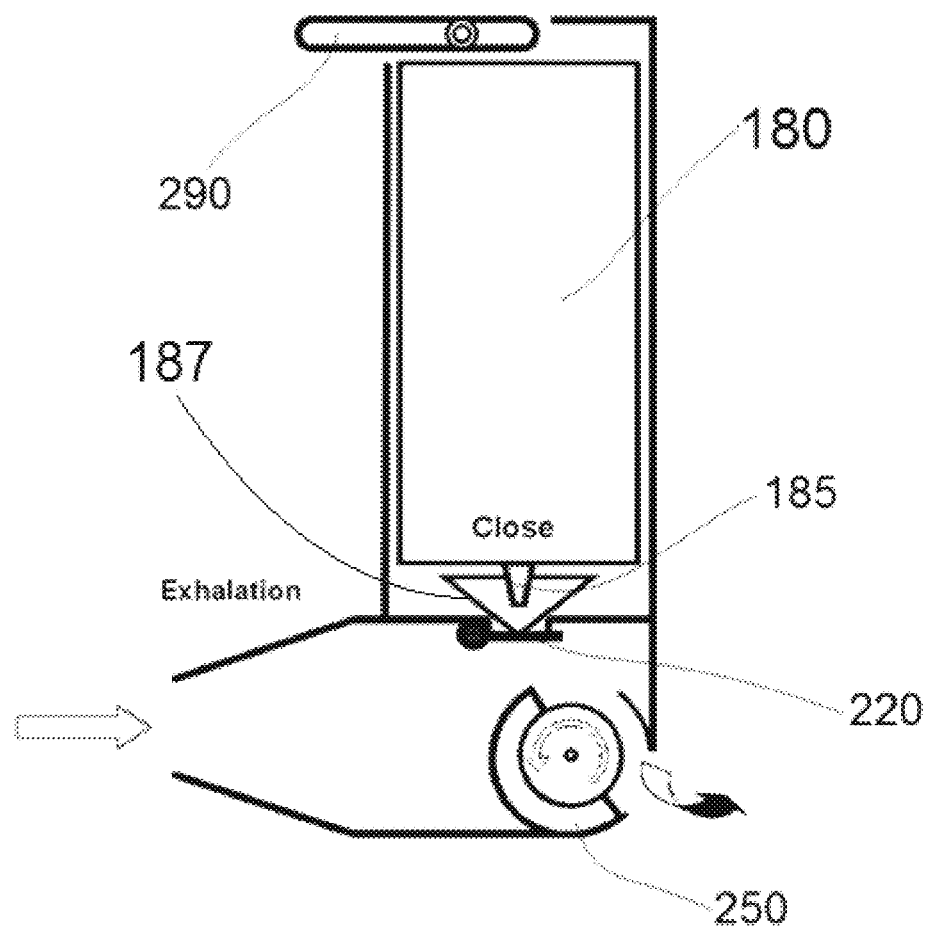
FIGS. 6a and 6b schematically illustrate a further embodiment of the device which is adapted to provide positive and negative pressure pulses which may be introduced into the airways by means of the same rotating disc at expiration and inspiration phases, respectively.
Figure 6B:
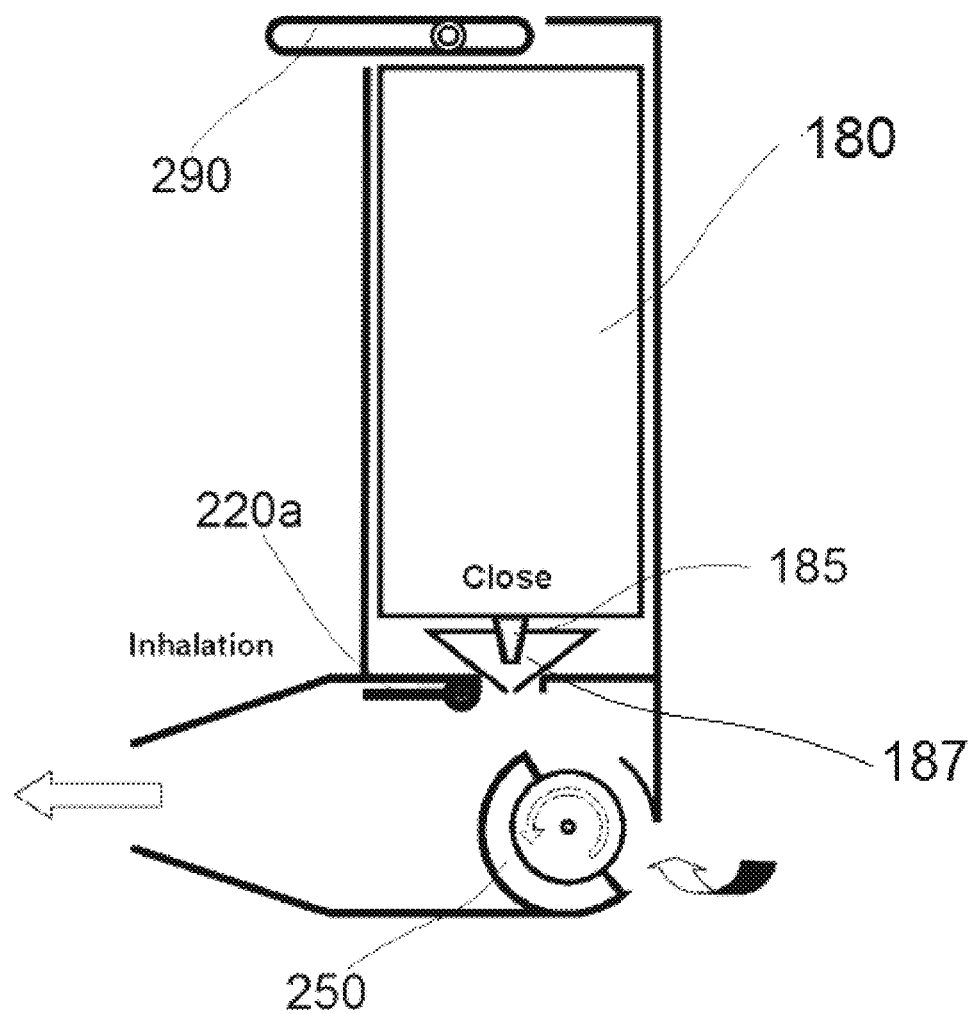

As shown in FIGS. 6a and 6b, both positive and negative pressure pulses may be introduced into the airways by means of the same rotating disc 250 of the device, which periodically blocks the inlet or outlet of air to or from the device. the device is provided with handle 290 configured to depress container 180 accommodating medicine such that the aforesaid medicine is dispensed into the air stream. During exhalation (see FIG. 6a), drug releasing mechanism (shutter) 220 is closed, so that the exhaled pulses of air are not mixed with a drug. In FIG. 6b, during inhalation, drug releasing mechanism (shutter) 220a is opened, so that a drug can be supplied to the patient with the pulses of air.

Figure 7A:
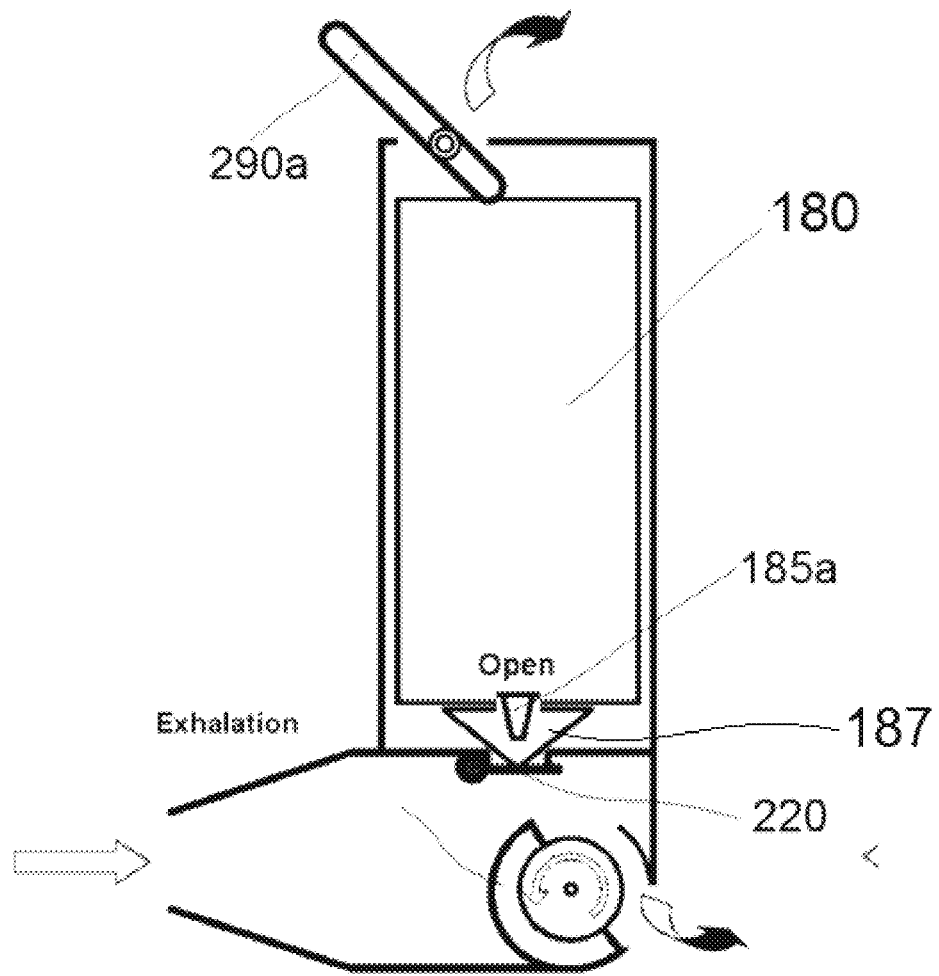
FIGS. 7a and 7b schematically illustrate a further embodiment of the device of FIGS. 6a and 6b in a 'drug delivery mode' in which medicament is introduced into the air stream at expiration and inspiration phases, respectively.
Figure 7B:
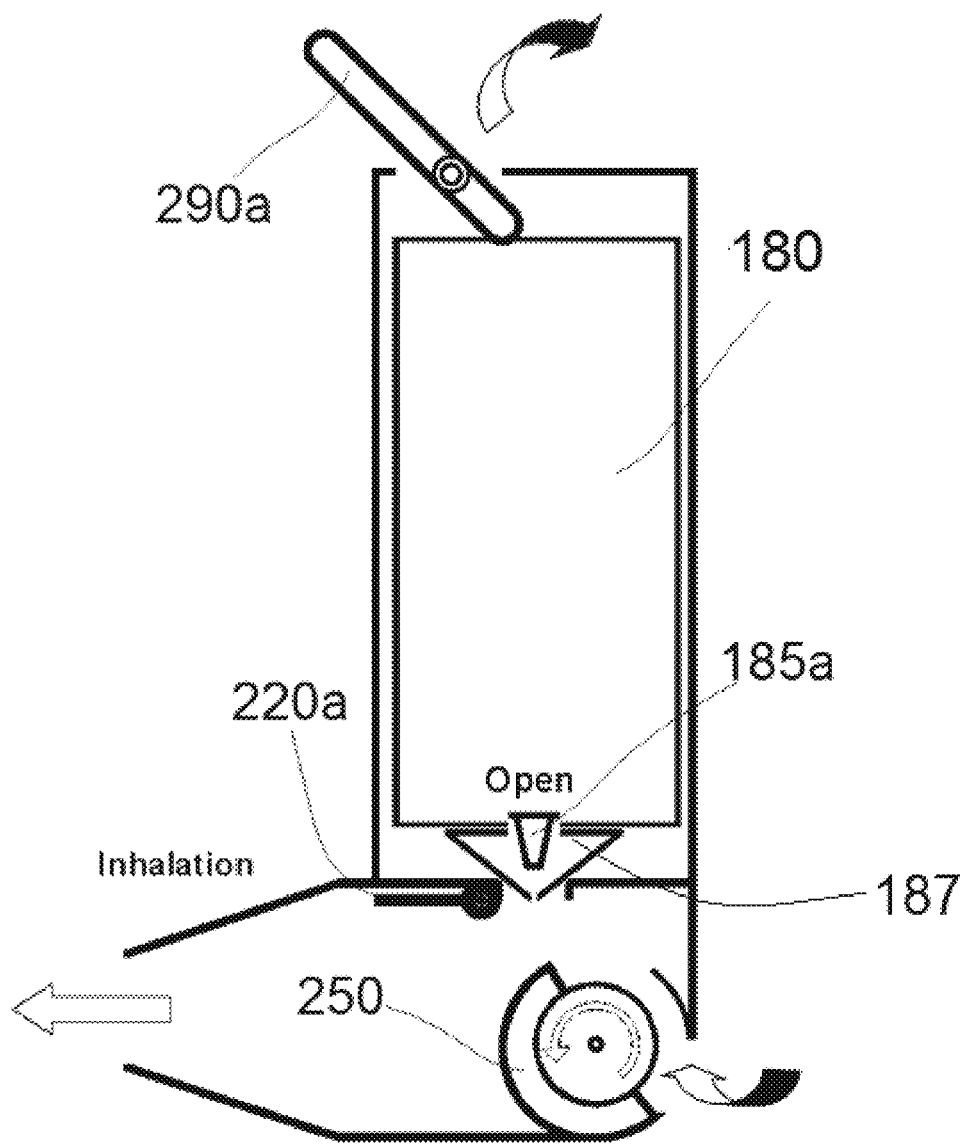

FIGS. 7a and 7b illustrate 'drug delivery mode' in which medicament is introduced into the air stream. Again, both positive and negative pressure pulses may be introduced into the airways by means of the same rotating disc of the device, which periodically blocks the inlet or outlet of air to or from the device. By pressing handle 290, the medicine container 180 is pushed down. Drug releasing mechanism 220 is adapted to deliver the drugs from container to the stream of fluid (and thereby to the user). Drug releasing mechanism 220 can be in two configurations: a closed position in which the drug is not released from container 220 (FIG. 7a) and an opened configuration in which the drug is delivered from container 220a.

Figure 8A:
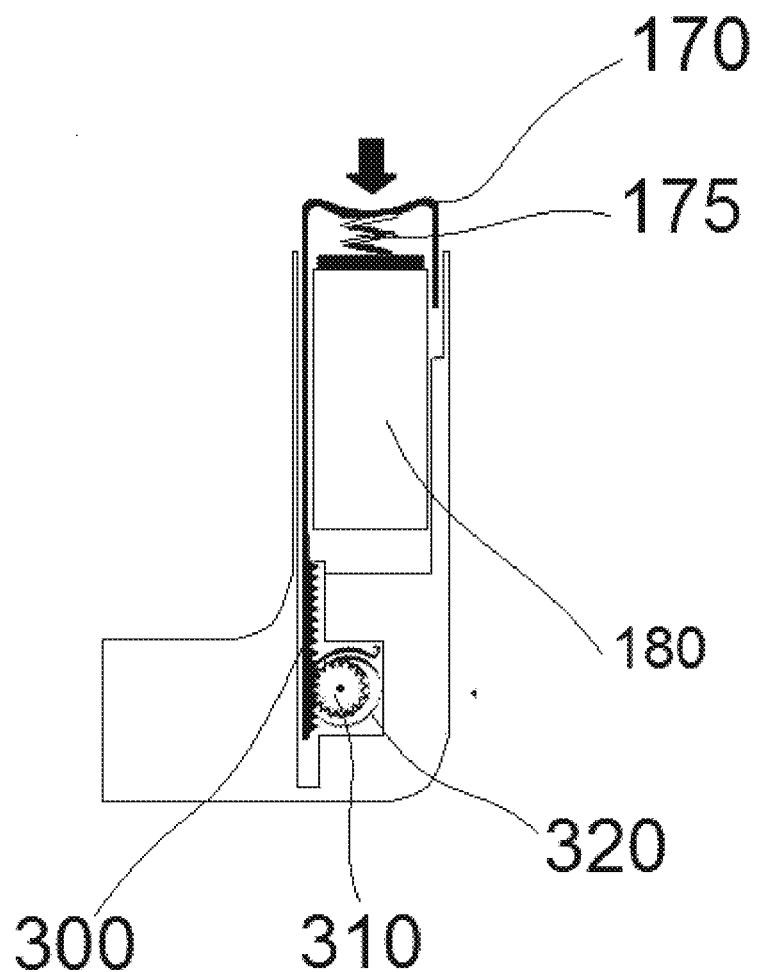
FIG. 8a schematically illustrates a further embodiment of the device with a container which is depressed by means of a spring-operated rack-and-pinion mechanism.
Figure 8B:
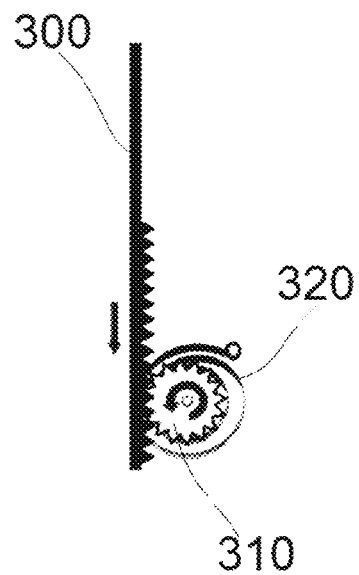
FIG. 8b is an enlarged schematic view of the spring-operated rack-and-pinion mechanism.
Figure 8C:
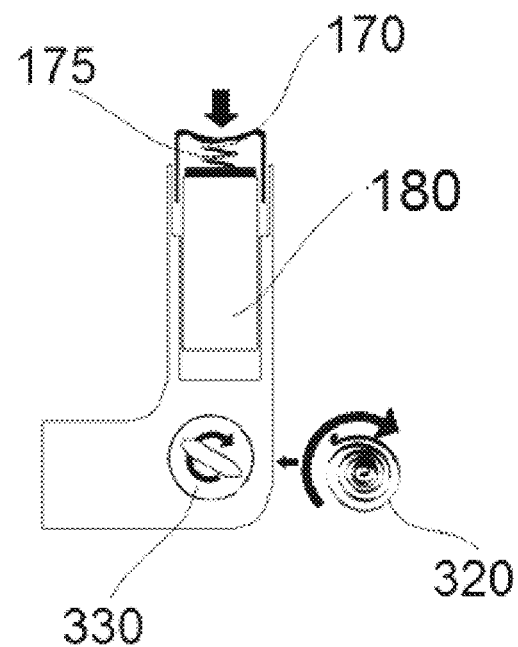
FIG. 8c is a partial external view of the device with a container which is depressed by means of a spring-operated rack-and-pinion mechanism.

In FIGS. 8a to 8c, another embodiment of the invention is shown. Container 180 is depressed by means of a spring-loaded rack and pinion gear. Specifically, spring 320 rotates pinion 310 meshed with rack 300. Spring 320 is tightened up by handle 330.

Figure 9A:
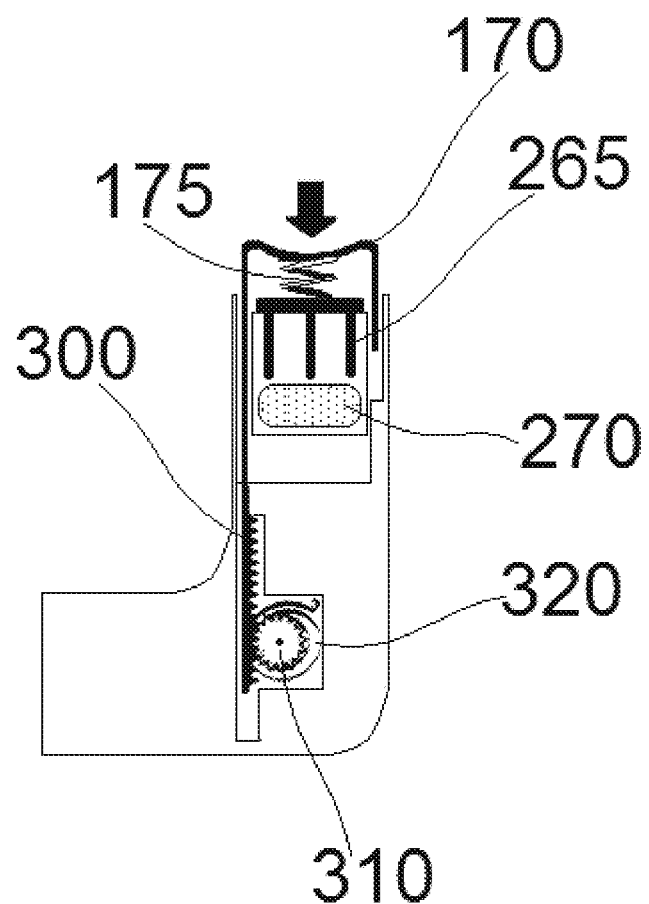
FIG. 9a schematically illustrates a further embodiment of the device with a rack-and-pinion gear activated when the inhaler cartridge is depressed.
Figure 9B:
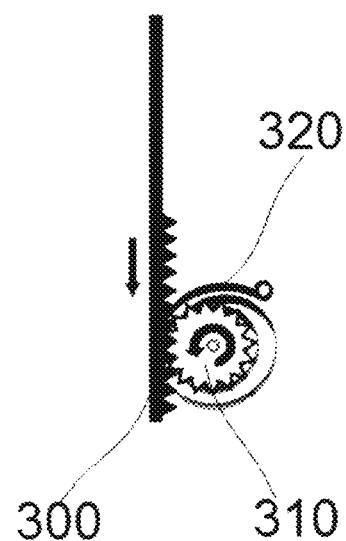
FIG. 9b is a partial external view of the device with a container which is depressed by means of a spring-operated rack-and-pinion mechanism.
Figure 9C:
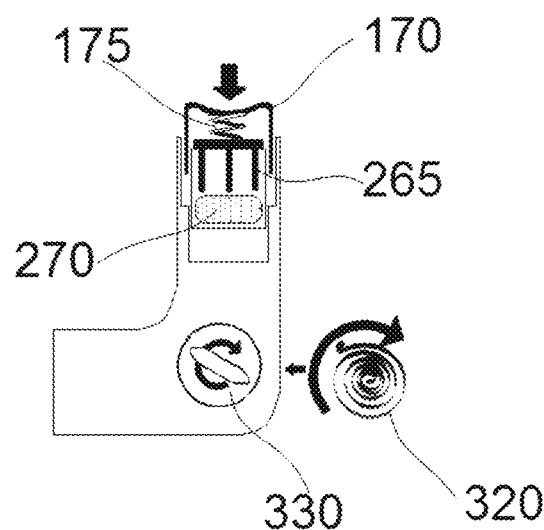
FIG. 9c is a partial external view of the device with a cartridge which is depressed by means of a spring-operated rack-and-pinion mechanism.

In FIGS. 9a to 9c another embodiment of the invention is shown wherein a rack- and pinion gear are activated when the inhaler cartridge (capsule) 270 is pierced by piercing member 265. This coils a spring that stores energy which can be used at a later time, for instance to actively rotate the disc 250 independent of the respiratory cycle phase (inspiration or expiration).

Figure 10A:
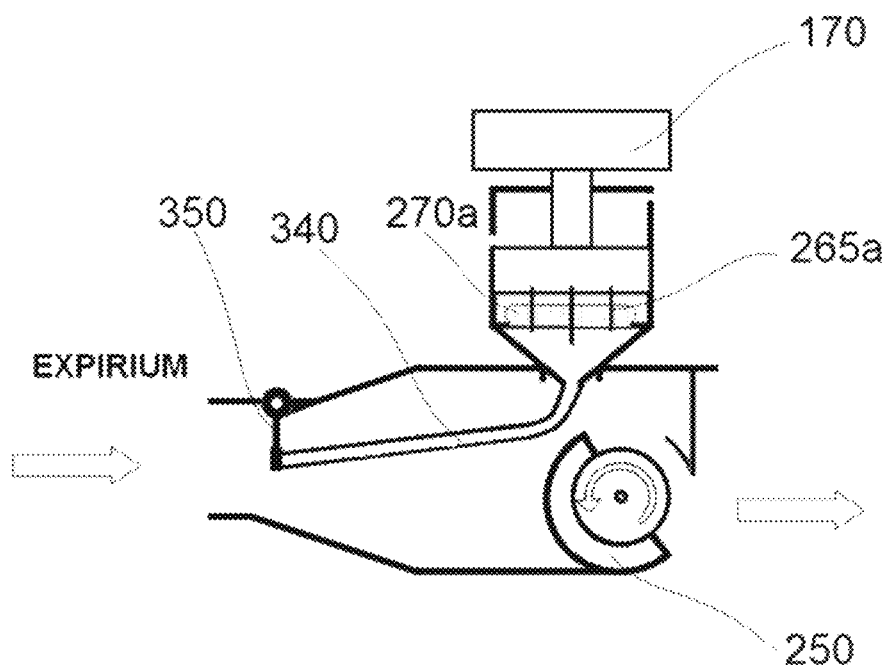
FIGS. 10a and 10b schematically illustrate a further embodiment of the device in which a dry powder lozenge is used instead of a pressurized canister at expiration and inspiration phases, respectively.
Figure 10B:
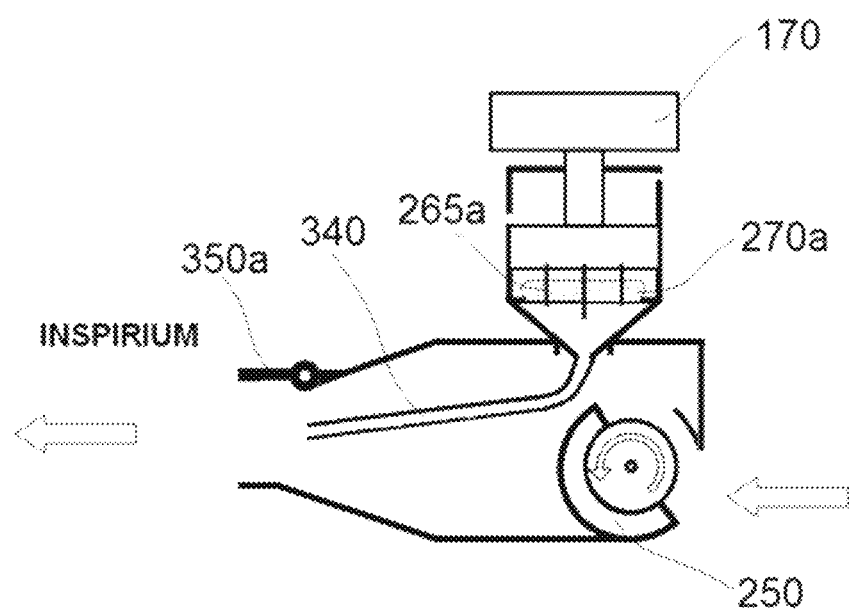

In FIGS. 10a and 10b, small flap 350 is used to block the egress of drug supply tube 340. This flap 350 operates independently of the rotating disc 250. Numerals 350 and 350a refer to closed (FIG. 10a) and open (FIG. 10b) positions, respectively. As shown in the figure, a spring, motor, or other device can be used to turn the disc 250 which is used to periodically block the inlet/outflow of fluid into/out of the device.

Figure 11:
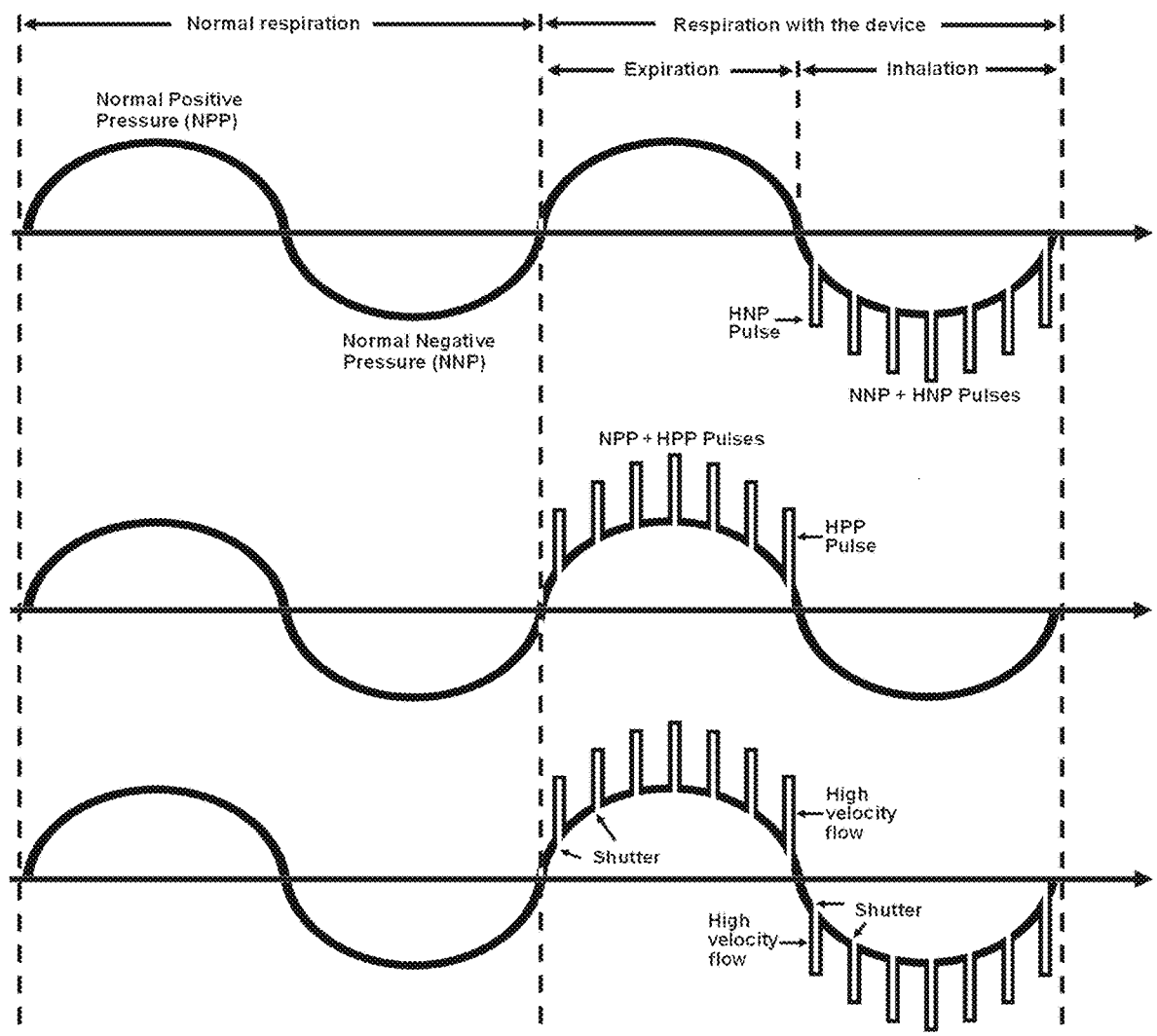
FIG. 11 schematically illustrates a plot of pressure vs. time is shown in qualitative detail for several embodiments of the current invention.

In FIG. 11, a plot of pressure vs. time is shown in qualitative detail for several embodiments of the current invention. As can be seen from the figure, upon a periodic pressure fluctuation such as a sine wave, a further modulation is introduced, such as a series of positive-going or negative-going square waves of a fixed frequency.

Figure 12A:
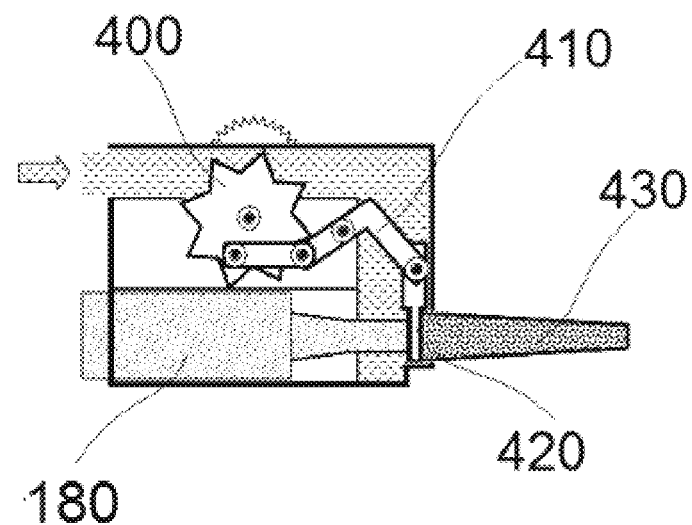
FIGS. 12a and 12b schematically illustrate further embodiments of the device which is intended for sinusitis patients and provided with a medicine container and cartridge, respectively.
Figure 12B:
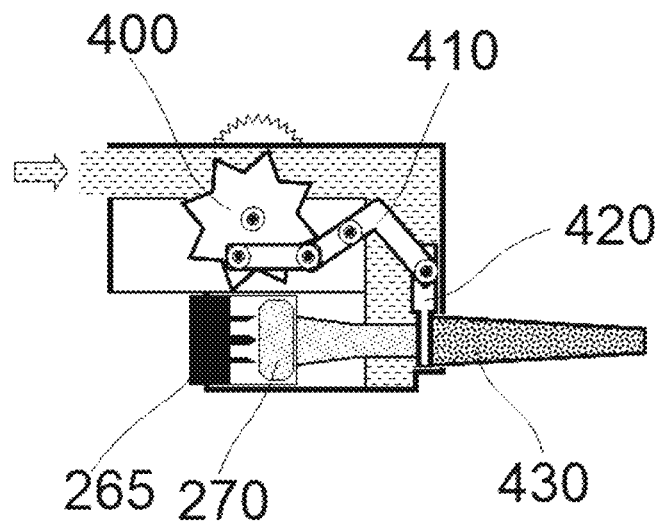

In FIGS. 12a and 12b, an embodiment of the device is shown that is intended for sinusitis patients. Here instead of a mouthpiece, nosepiece 430 is used that can be employed to introduce pressure fluctuations and/or medication into the nostril. Turbine wheel 400 driven by inhaled/exhaled air is mechanically interconnected with air shutter 420 by means of lever 410. Shutter 420 blocks and releases air flow with rotation of turbine wheel 400. FIG. 12a corresponds to a closed position of shutter 420, while FIG. 12b to an open position.

Figure 13A:
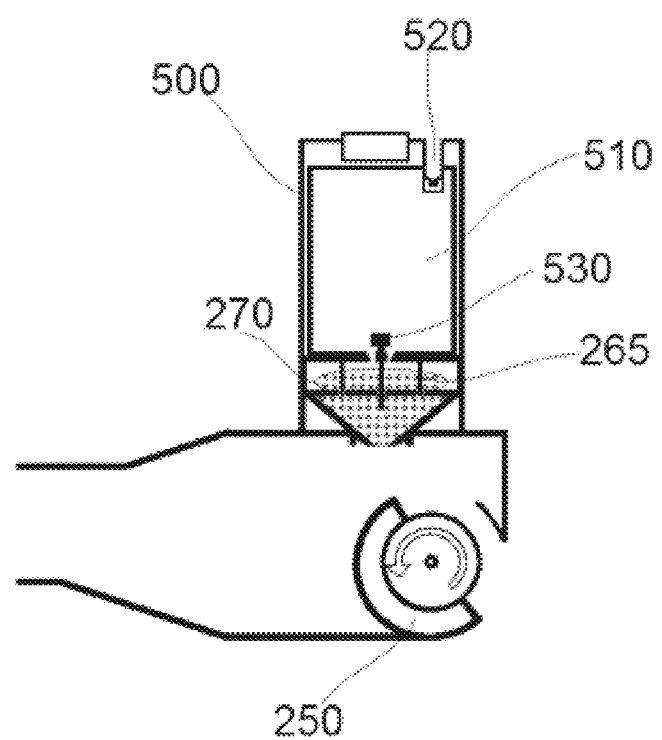
FIG. 13a schematically illustrates a further embodiment of the device with a high pressure canister.
Figure 13B:
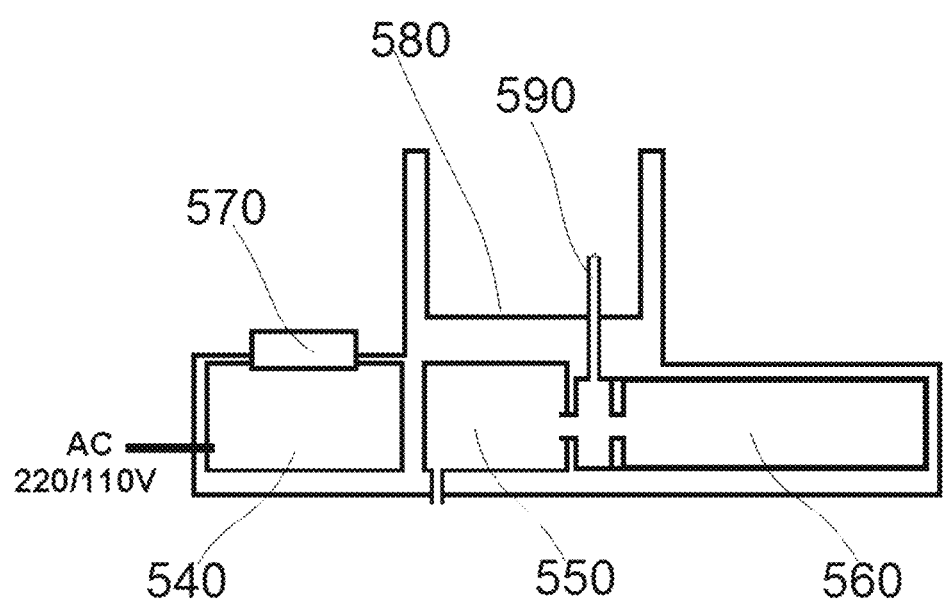
FIG. 13b schematically illustrates an air pump.
Figure 13C:
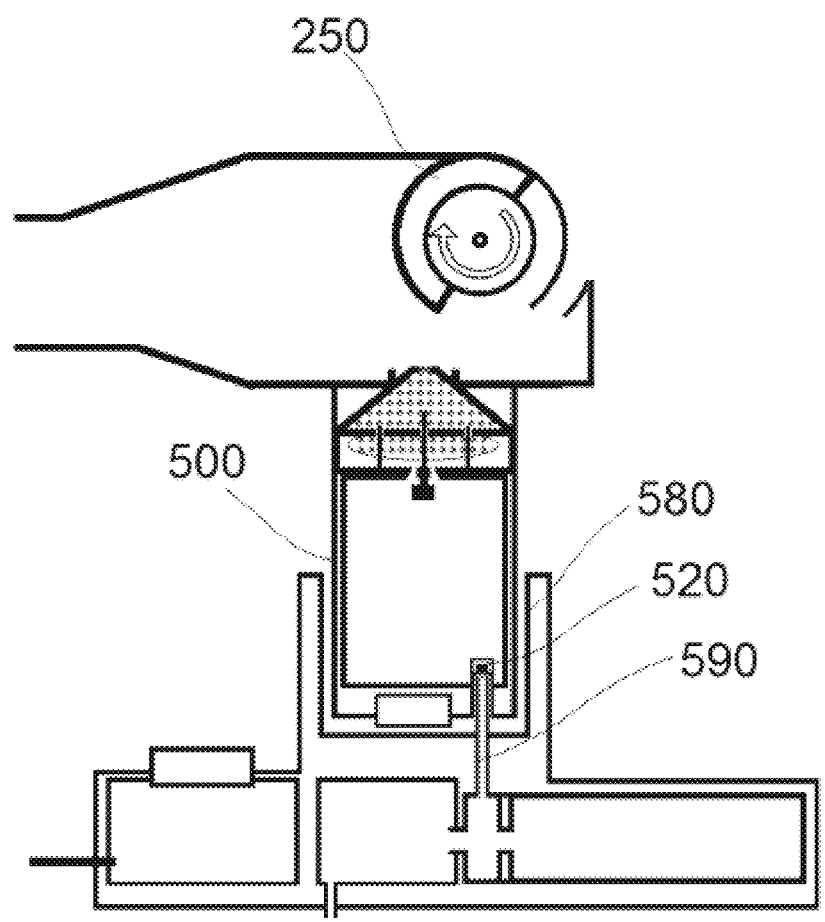
FIG. 13c schematically illustrates the device with a high pressure canister connected to the air pump.

In FIGS. 13a to 13c, another embodiment of the device is shown where a high-pressure canister and air pump is used. This embodiment may use an inhaler loading station at which the inhaler is loaded with pressurized fluid such as air that may contain medications or other fluids. Specifically, as shown in FIG. 13a, canister 510 is within housing 500. Pressurized gas is dispensed via valve 530. A device for refilling canisters is presented in FIG. 13b. The device comprises power supply and control unit 540 with on/off button 570, high-pressure pump 560 and pressure reduction valve 550.

The refilling device with the inhaler to be refilled is shown in FIG. 13c. The canister 510 (not shown) is inserted into mounting seat 580 and filling pipe 590 is inserted into fill valve 520.

Figure 14A:
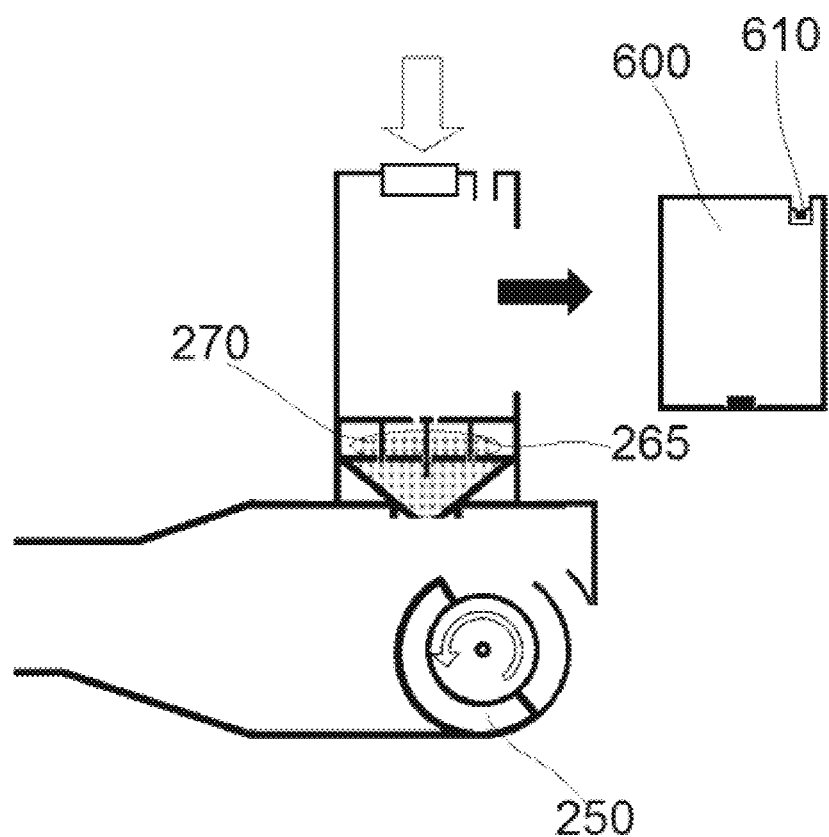
FIG. 14a illustrates a further embodiment of the device with a replaceable high pressure canister.
Figure 14B:
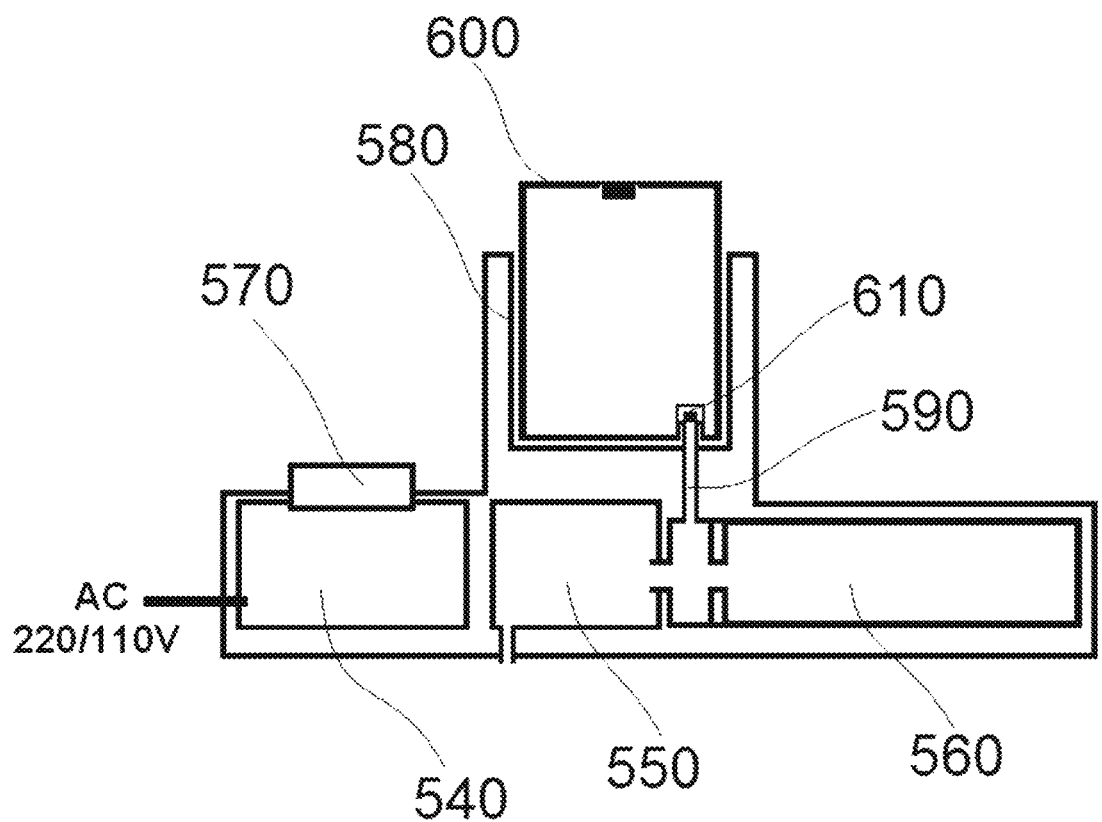
FIG. 14b schematically illustrates an air pump with a replaceable high pressure canister connected thereto.

In FIGS. 14a and 14b, another embodiment is shown with a container loading station is shown. The container loading station is adapted to fill a removable container 600 having fill valve 610 with high pressure air or other fluid.

Figure 15A:
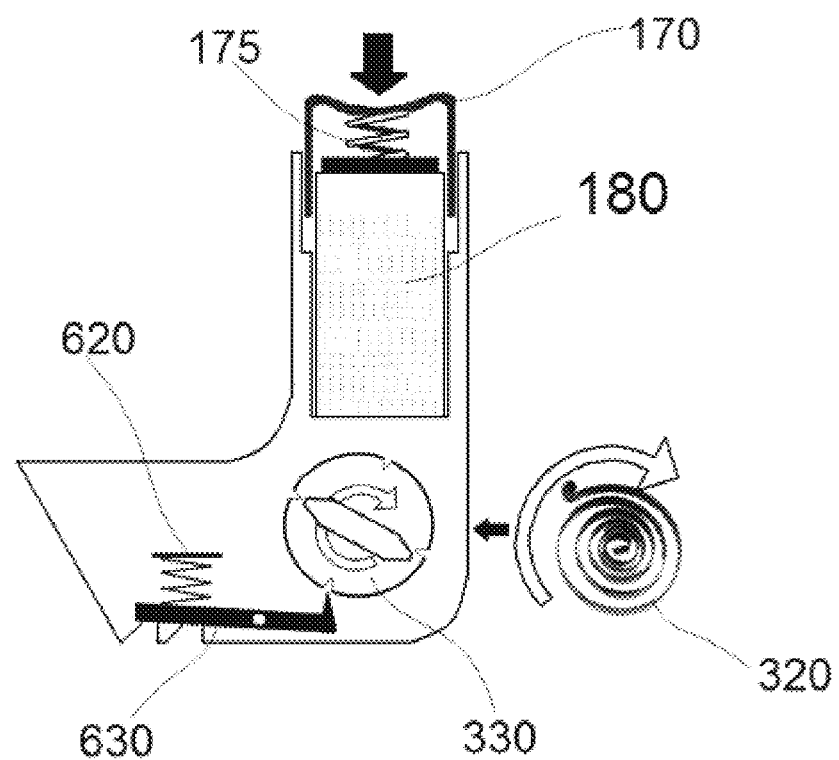
FIG. 15a schematically illustrates a further embodiment of the device with a spiral spring loading mechanism and a medicine container.
Figure 15B:
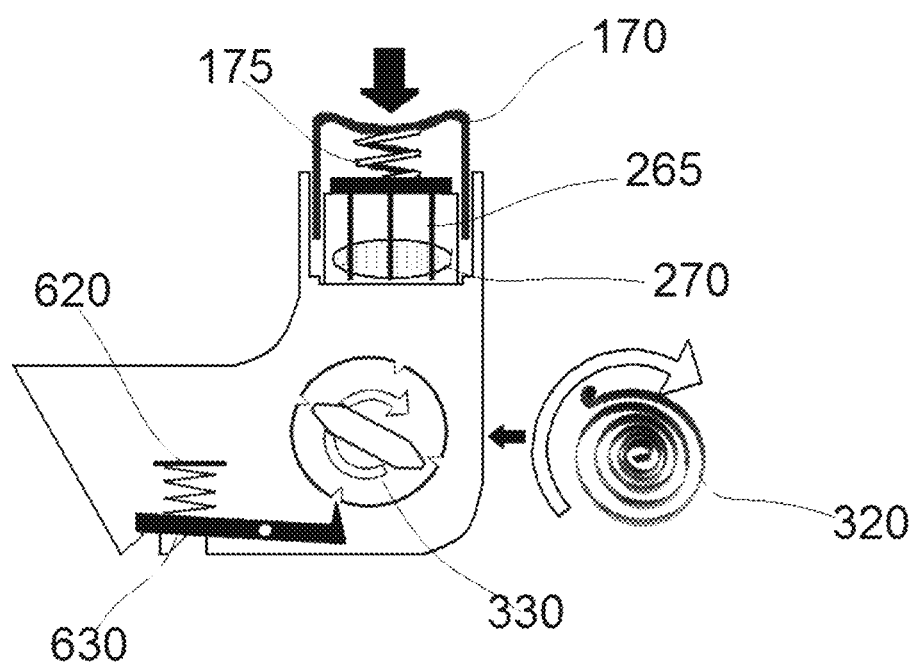
FIG. 15b schematically illustrates a further embodiment of the device with a spiral spring loading mechanism and a pierceable capsule.
Figure 15C:
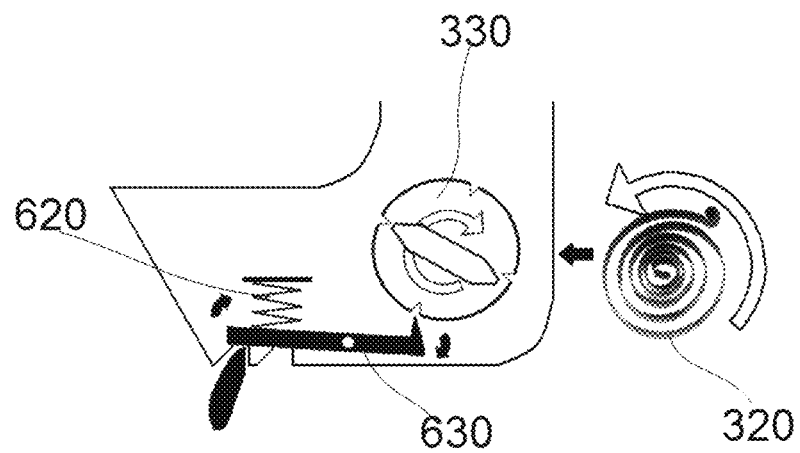
FIGS. 15c and 15d and schematically illustrate a blocking lever mechanism in free and engaged positions, respectively.
Figure 15D:
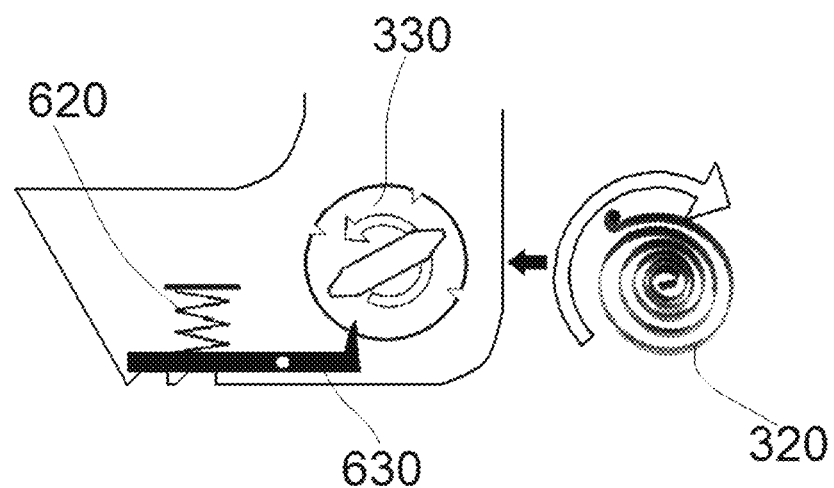

In FIGS. 15a to 15d, a series of figures is shown that illustrate the spiral spring loading mechanism of the device. This mechanism employs a ratchet mechanism to periodically engage lever 630 loaded by spring 620. Spiral spring 320 of the device here is activated by means of a ratchet and pawl mechanism, whose pawl is lifted by means of the user's teeth or lips. FIGS. 15a to 15b depict embodiment with medicine container 180 and pierceable capsule 270, respectively. FIGS. 15c to 15d show two positions of lever 630 releasing and blocking the rotatable member 330.

Figure 16:
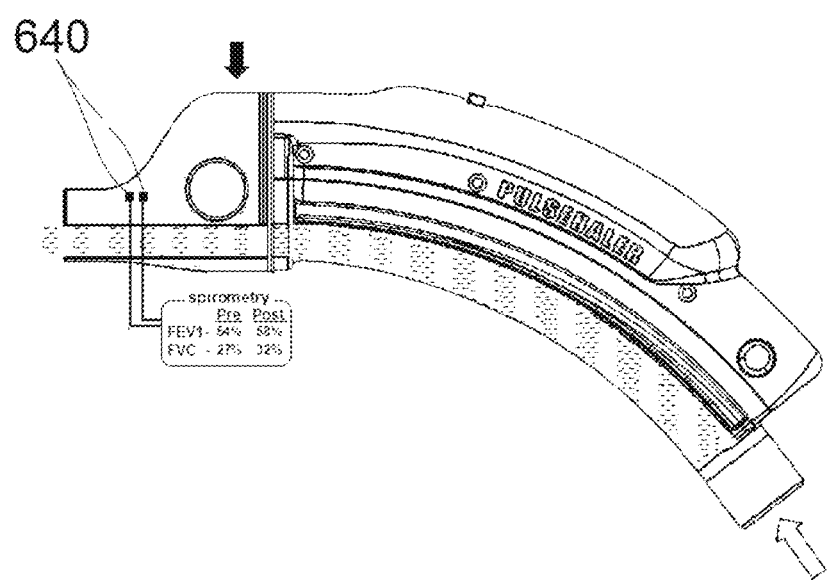
FIG. 16 schematically illustrates a further embodiment of the device with a mouthpiece, a base unit, and a spirometric sensor.

In FIG. 16 an embodiment of the device is shown that employs a sensor 640 for spirometry (breath measurements such as inhalation/exhalation flow rate, pressure, vital capacity, etc.) This can be used to give the user feedback, which can often motivate the user to use the device more effectively and/or more often such that the treatment is rendered more effective.

In certain embodiments of the device, the act of depressing a canister or other lever on the device will cause the periodic blockage and passage of fluid through the device; for example one possible mechanism may utilize a gearwheel and cam adapted to convert rotational into linear motion of a fluid-blocking gate or door. Obviously a rack-and-pinion mechanism could also be used, as could a variety of other mechanisms that will be obvious to one skilled in the art.

Figure 17A:
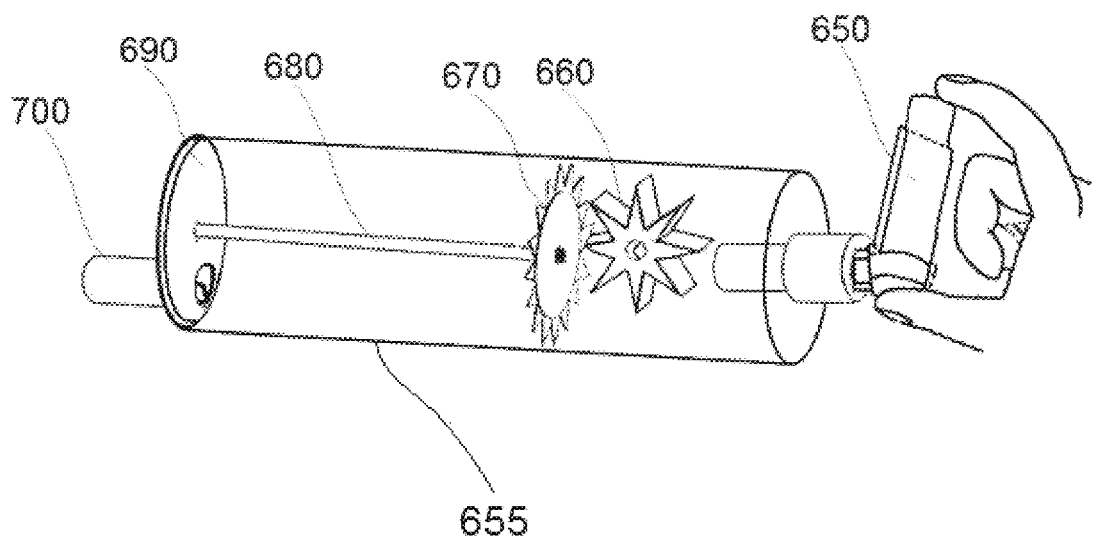
FIG. 17a schematically illustrate a further embodiment of the device with an inhaler connected to a spacer provided with a turbine wheel.
Figure 17B:
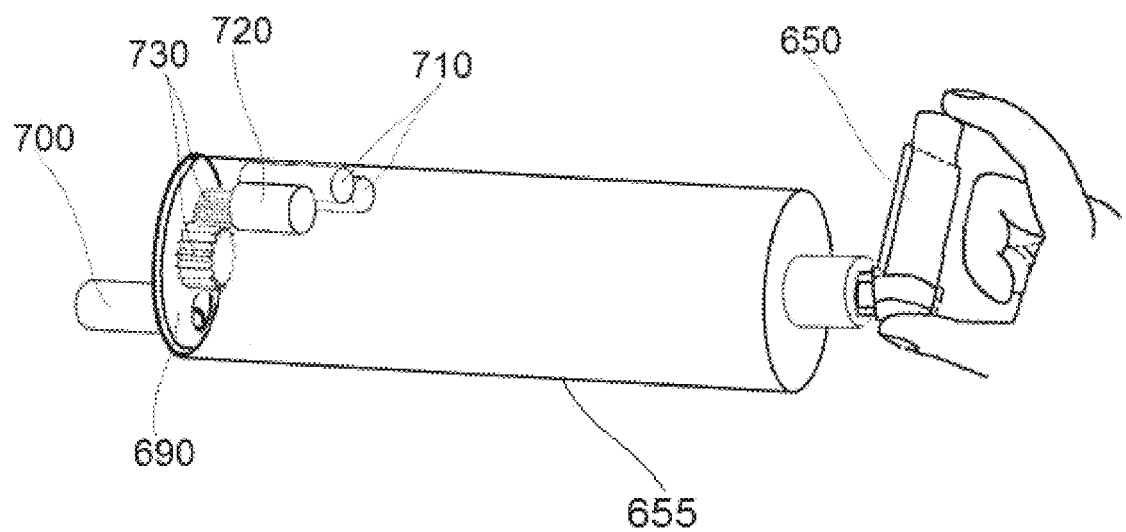
FIG. 17b schematically illustrates a further embodiment of the device with an inhaler connected to a spacer provided with an electric motor.

Reference is now made to FIGS. 17a and 17b, which schematically illustrates another embodiment of the present invention. According to this embodiment, the device disclosed by the present invention, is a constructed of a known in the art inhaler 650 connected to spacer 655. Inhaler 650 comprises at least one container for storing said drugs, and a drug releasing mechanism for delivering the drugs from the container to the user through spacer 655. The aforesaid spacer presented in two embodiments. In FIG. 17a, spacer 655 comprises turbine wheel 660, cogwheel 70, transmission shaft 680 and shutter disc 690 which intermittently blocks and releases air flow from inhaler 650. In FIG. 17b, shutter disc 690 is rotated by electric motor 720 energized by batteries 730. Numeral 730 refers to intermediate gears.

Spacer 123 comprises an air controlling mechanism 130 for controlling passage of air during inhalation or exhalation.

Figure 18A:
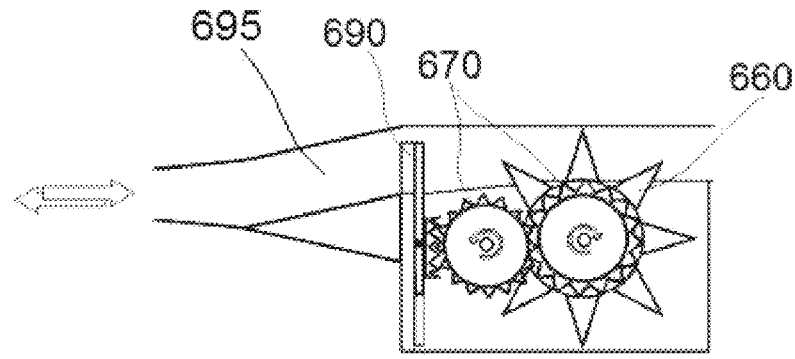
FIGS. 18a and 18b illustrate further embodiments of the device with an exemplar breath-operating rotating mechanism including three and two cowheels, respectively.
Figure 18B:
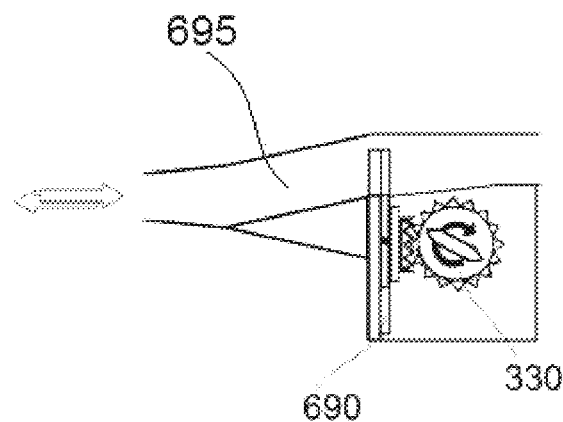
Figure 18C:
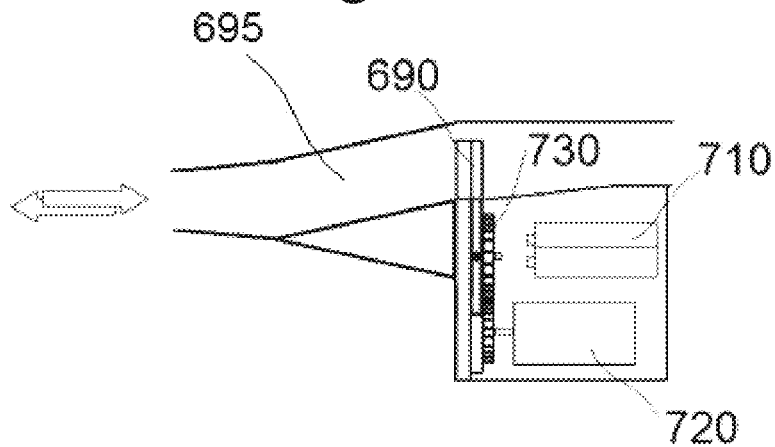
FIG. 18c schematically illustrates a further embodiment of the device with an exemplar electrically operating mechanism.

Reference is now made to FIGS. 18a to 18c, which schematically illustrates different embodiment of a rotating mechanism for the air controlling mechanism 130. According to FIG. 18a, the rotation may be actuated by the inspiration or the expiration itself. In other words, when the user inhales or exhales air and the air itself rotates a turbine wheel 660 which causes the closing/opening of passage 695. According to another embodiment (see FIG. 18b), the rotation may be performed by any known in rotating mechanism 330, which may also be connected to a spring (not shown). The operation of passage 151 causes temporal blockage of air passage which result in pulse of air. These pulses may be Negative Pressure (NP) pulses, and Positive Pressure (PP) pulses during inhalation or exhalation of air.

According to another embodiment, the air controlling mechanism may be driven by manual rotation of switch 330 which provides potential energy to a spring (not shown), so as to control the closing/opening of passage 695 while the potential energy of spring is released.

According to another embodiment, the air controlling mechanism may be driven by electric motor 720 energized by batteries 710, so as to control the closing/opening of passage 695.

According to the embodiment of FIG. 23, the passage of air in each pulse may be provided only when aperture 159 and the mouthpiece of the device are fluidly connected to each other.

Figure 19A:
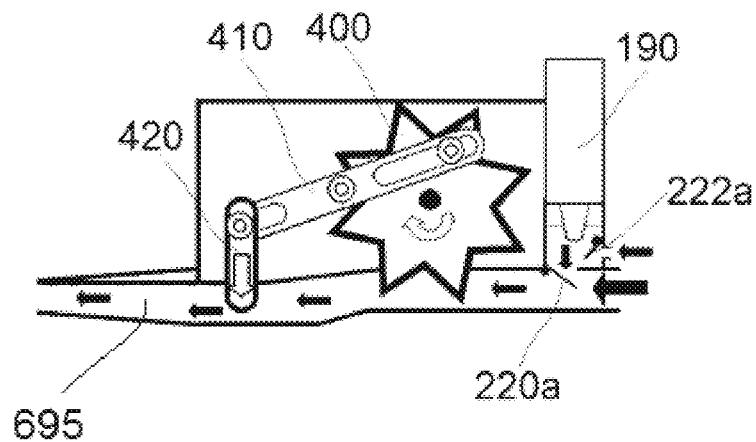
FIGS. 19a and 19b schematically illustrate a further embodiment of the air controlling mechanism provided a shutter driven by a lever mechanism in open and close positions, respectively and at the inhalation phase.
Figure 19B:
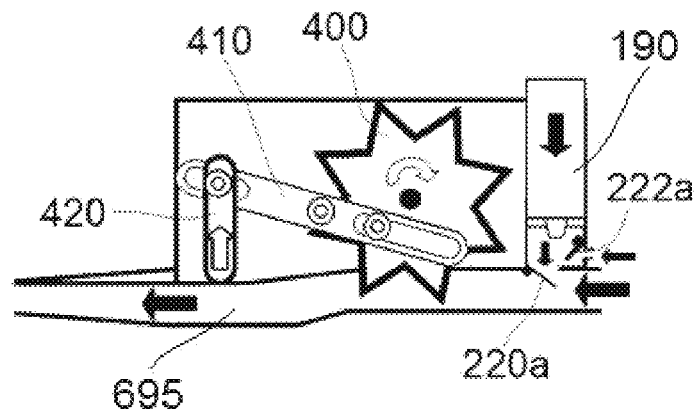
Figure 19C:
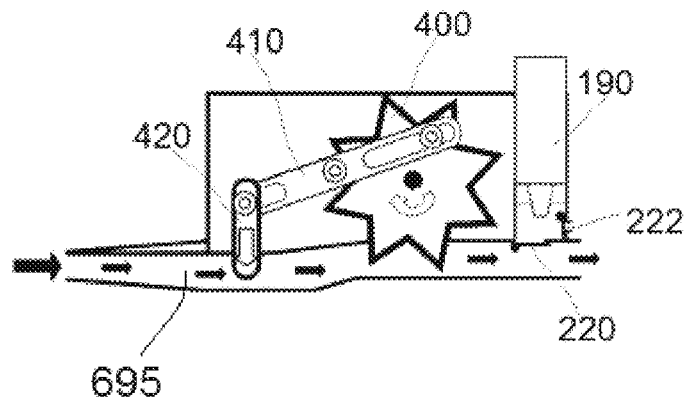
FIG. 19c schematically illustrates a further embodiment of the air controlling mechanism provided a shutter driven by a lever mechanism in close position at the exhalation phase.

Reference is now made to FIGS. 19a to 19c, which schematically illustrate another embodiment of the air controlling mechanism. According to this figure, the air controlling mechanism comprises a rotating cogwheel 400, the rotation of which is actuated by the passage of air within a tubule 695. Each rotation of cogwheel 400 is translated into opening and closing of shutter 420. This translation of the rotational movement to the longitudinal movement is performed via arm 410.

It should be mentioned the according to this embodiment, the shutter 420 is not closed till the end, so as to provide passage air which rotates cogwheel 400.

The device of this embodiment may be used with drug and without drug. When a drug is used, there is a mixture of the air with the drug, and each pulse comprises a pulse of air with a drug. The device of this embodiment may also be actuated in inspiration and expiration, while Negative and Positive Pressure pulses are generated.

Figure 20A:
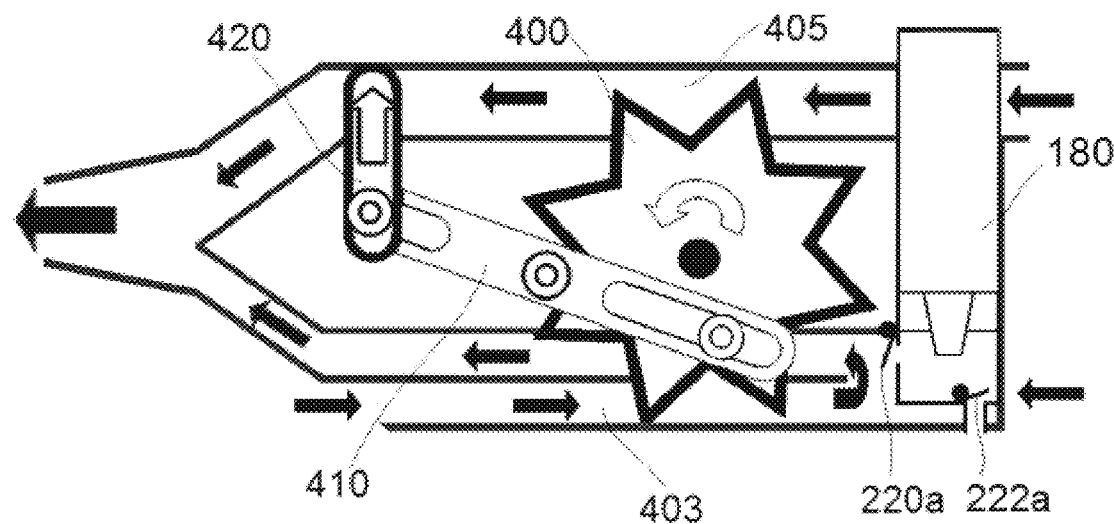
FIGS. 20a and 20b schematically illustrate a further two-passage embodiment of the device at inhalation phase in closed and open positions, respectively.
Figure 20B:
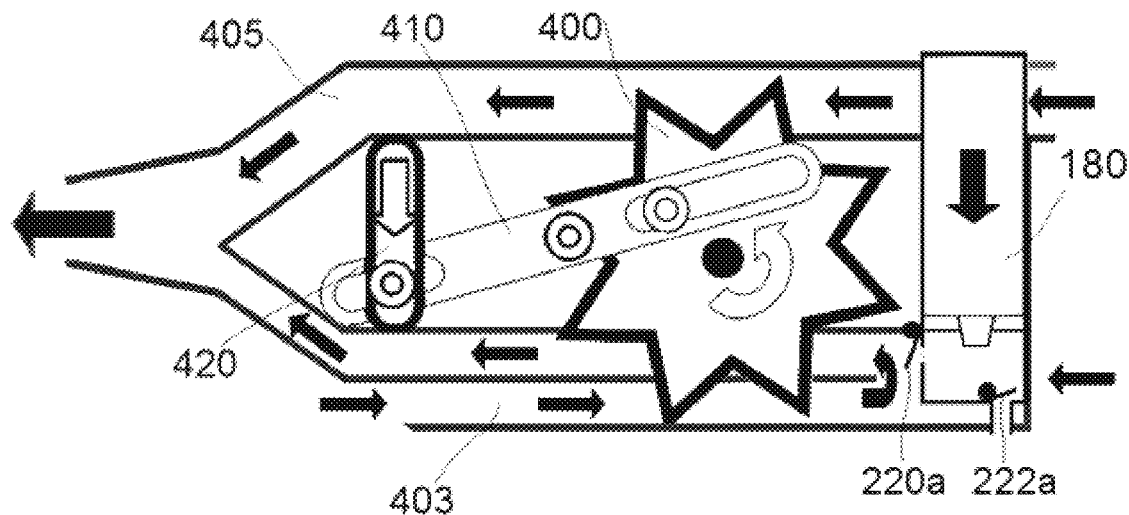

Reference is now made to FIGS. 20a and 20b, which schematically illustrates another embodiment of the device with a cogwheel 400 at the inhalation phase. According to this embodiment, the device comprises two channels: one channel 403 for providing passage of air which rotates the cogwheel, and another channel 405 which has a shutter for blocking the passage of air. FIGS. 20a and 20b correspond to closed and open positions of air shutter 420, respectively.

According to this embodiment, the drug is provided from container 180 through open drug shutter 220 and mixed with the air by via channel 403. Open shutter 222a enables flowing the outer air into channel 403 being mixed with the drug. Therefore, the drug is provided to the user in a continuous manner.

Figure 21A:
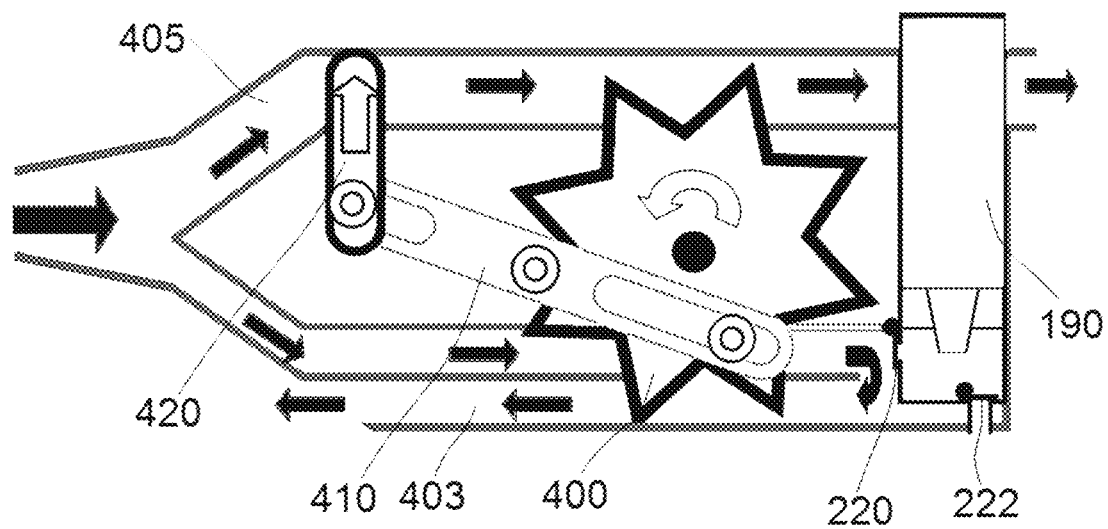
FIGS. 21a and 21b schematically illustrate a further two-passage embodiment of the device at exhalation phase in closed and open positions, respectively.
Figure 21B:
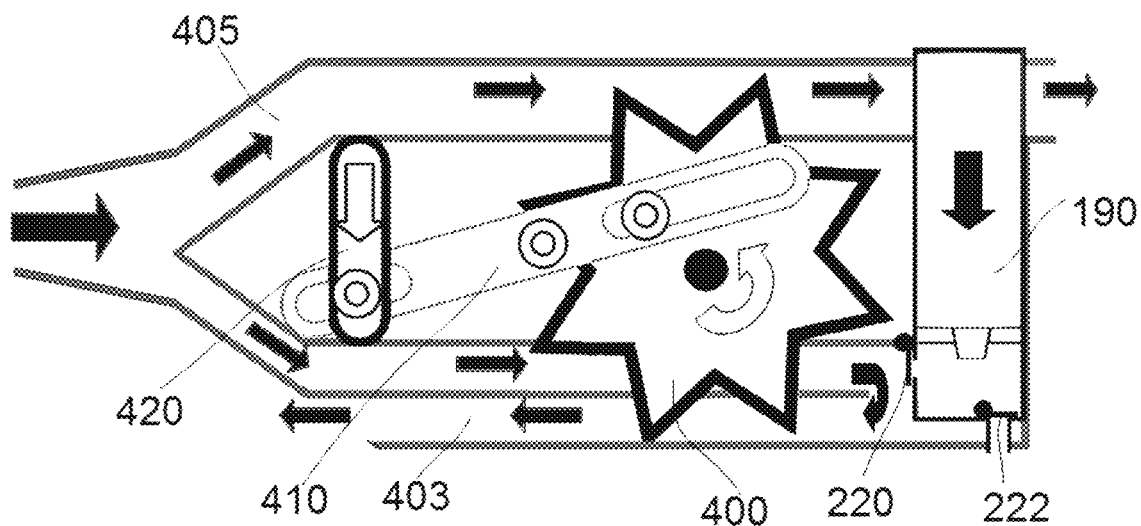

According to the embodiment of FIGS. 21a and 21b, the device with cogwheel may be actuated by expiration air flow (with/without a drug). At the expiration phase, shutters 220 and 222 are closed. FIGS. 21a and 21b correspond to closed and open positions of air shutter 420, respectively.

According to another embodiment of the device with a cogwheel, the air controlling mechanism is adapted to generate pressure pulses of Negative Pressure and/or Positive Pressure into the respiratory system during inspiration and/or expiration, and the drug releasing mechanism is adapted for entraining the drugs into the pressure pulses, such that uptake of the drugs by the tissues of the respiratory system is facilitated. The pressure pulses may be selected from the group consisting of: inspiratory Negative Pressure (NP) pulses, inspiratory Positive Pressure (PP) pulses, expiratory Negative Pressure (NP) pulses, expiratory Positive Pressure (PP) pulses into said respiratory system, and any combination thereof.

Figure 22A:
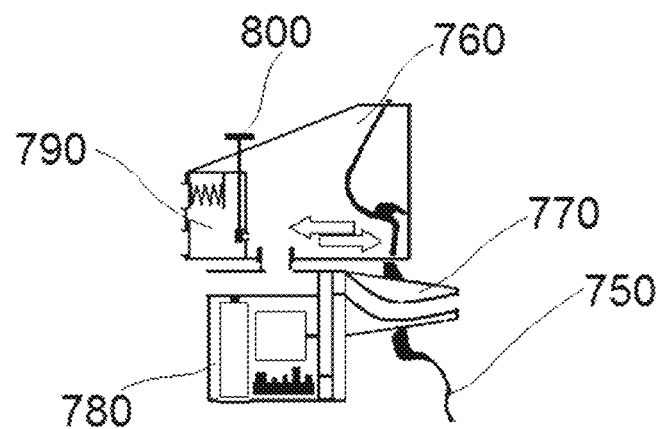
FIGS. 22a and 22b schematically illustrate a device of the present invention for treating sinusitis per se and the aforesaid in use, respectively.
Figure 22B:
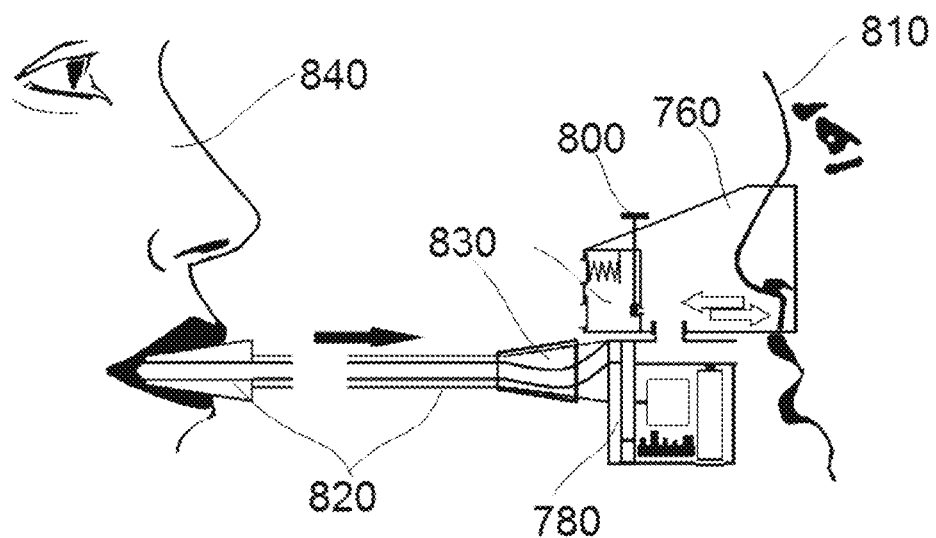

Reference is now made to FIGS. 22a and 22b which schematically illustrate another embodiment of the device of the present invention. The device may treat common ear, nose, and throat problems. These problems may sometimes cause pain in the ear and/or headache, and also other symptoms. These problems include impacted wax, ear canal infection (otitis externa) of bacterial or fungal etiology, middle ear infection (otitis media), etc.

According to the embodiment in FIG. 22a, the device comprises a nosepiece 760 which may be fluidly connected to mouthpiece 770 connectable to nostrils and mouth of user 750. The device may be operated by the user himself. The user may inhale or exhale air through the device, and the device may generate pulses of air. These pulses may be Negative Pulses or Positive pulses. The air controlling mechanism 780 of this embodiment may be a spinning disk with a hole. According to other embodiment, air controlling mechanism 780 may be a shutter as described above. The spinning disk may be actuated by an electrical power by batteries. FIGS. 22a and 22b illustrate two different embodiments of the present invention in which the air controlling mechanism 780 may block and unblock passage of air only to the mouth of the user, and another embodiment in which the air controlling mechanism 780 may block and unblock passage of air to the mouth and to the nose at the same time. The device may also comprise a container 790 with a drug which may be activated and deactivated according to the special needs of the user. In case of a need for treating to nasal passages with a drug, the container will be supplied and actuated. The actuation of the container may be performed by drug releasing mechanism 800 which is adapted to deliver the drugs from container 790 to user (to his mouth/nose, or both of them).

By using the device of FIG. 22a, the user may inhale and exhale air through nosepiece 760 and mouthpiece 770 at the same time. By using the device, the user himself may determine the pressure and the capacity of the generated air pulses. This may depend of the strength of the inhalation and exhalation. The frequencies of air controlling mechanism 780 may be different according to the special treatment needs.

According to one embodiment of the present invention, the device may be actuated without drugs. The pulses which are generated by the device of FIG. 22a cause different mechanical and other effects in the tissue of the user within the nasal passages. For example, the pulses may open a blockage which is located within the sinus and captures the inflammation within the sinus. Negative Pressure pulses are able to generate vacuum effect within the nose of the user. This may move the cilia within the nasal passages, and transport the inflammation out of the sinus. Positive Pressure pulses may generate widening of the nasal passages which may transport the inflammation out of the sinus.

FIG. 22b additionally illustrates another embodiment of the preset invention in which a third party treatment may be provided to the user. The third party 840 may be a parent which inhales/exhales air through an extendable mouth piece 820. The extendable mouth piece 820 may be connected to the mouthpiece of the device. According to this embodiment, the third party treatment may be performed when the user is not able to perform by himself the inhalation/exhalation. The device of this embodiment may also be used in emergency cases, and with elderly people. The third party treatment may be useful for treating various problems with the sinus, the ears, the nose and the throat or the user.

According to some embodiments of the present invention, the pressure pulses are provided according to a treatment protocol which is adapted to increase the uptake of medications and/or to improve the clinical outcome of the treatment.

For purposes of the current invention, the terms 'protocol' or 'treatment protocol' or 'therapeutic protocol' refers hereinafter to a description of the therapeutic procedure unlimitedly defining frequency and amplitude of the provided fluid pressure pulses (FPP), treatment period, and medicines optionally inserted into the air flow.

According to some embodiments of the present invention, fluid pressure pulses (FPP) can be provided to the mouth cavity of a patient at a predetermined frequency according to a protocol of Table 1.

The treatment via the device of the present invention may be performed by delivering series of air packets (discrete wavetrains of different repetition frequencies and pulse amplitudes) according to predetermined protocols in Table 1. The frequencies may be electronically controlled. This ensures accurate frequency and pressure delivery of each air packet. The air packets are delivered for a pre-specified time period.

Without wishing to be bound by theory discrete wavetrains of different repetition frequencies and pulse amplitudes result in specific therapeutic effects on the various components of the lung tissue, e.g. Bronchial smooth muscles and blood vessels relaxation, mucus clearance of the airways, reduction of the pulmonary vascular pressure etc.

By using the device and the protocols of the present invention, and generating and delivering discrete wave trains of different repetition frequencies and pulse amplitudes, will increase the uptake of medications.

According to some embodiments, the present invention supplies fluid pressure pulses (FPP) to the mouth cavity of a patient at a predetermined frequency and pressure in a predetermined manner which is not dependent upon the natural breathing rate of the patient.

According to other embodiments, the protocols of the present invention are tailor made protocols for diseases such as: asthma, COPD, CF. Other diseases of the airway are within the scope of the present invention, as well. In accordance with proposed technical solution, the profile of the pressure comprises alternation of pneumatic pulse sequences of high and low amplitudes corresponding to inhalation and exhalation, respectively. Amplitude and repetition rate of the pneumatic pulses are preprogrammed by a patient or a doctor according to the treated disease.

TABLE 1

Therapeutic Protocols for Asthma, COPD and CF

| Disease | Step number | Frequency, Hz | Rpm of rotating disc | Duration, min | Remarks |
|---|---|---|---|---|---|
| Asthma | 1 | 60.0 ± 7.0 | 3600 ± 360 | 1.0 ± 0.1 | — |
| | 2 | 8.0 ± 0.9 | 480 ± 48 | 1.5 ± 0.15 | — |
| | 3 | 5.0 ± 0.6 | 300 ± 30 | 1.5 ± 0.15 | — |
| | 4 | 25.0 ± 3.0 | 1500 ± 150 | 2.5 ± 0.25 | — |
| | 5 | 0 | 0 | 1.0 ± 0.1 | Rest |
| | 6 | 13.0 ± 7.0 | 780 ± 78 | 1.5 ± 0.15 | — |
| | 7 | 7.0 ± 7.0 | 720 ± 72 | 1.5 ± 0.15 | — |
| | 8 | 0 | 0 | 1.0 ± 0.1 | Rest |
| | 9 | 34.0 ± 7.0 | 2040 ± 204 | 2.5 ± 0.25 | — |
| | 10 | 19.0 ± 7.0 | 1140 ± 114 | 3.0 ± 0.3 | — |
| | Total | | | 17 | — |
| COPD | 1 | 60.0 ± 7.0 | 3600 ± 360 | 0.5 ± 0.05 | — |
| | 2 | 5.0 ± 0.6 | 300 ± 30 | 3.0 ± 0.3 | — |
| | 3 | 7.0 ± 7.0 | 438 ± 42 | 2.0 ± 0.2 | — |
| | 4 | 0 | 0 | 1.0 ± 0.1 | Rest |
| | 5 | 13.0 ± 7.0 | 780 ± 78 | 3.0 ± 0.3 | — |
| | 6 | 34.0 ± 7.0 | 2040 ± 204 | 2.0 ± 0.2 | — |
| | 7 | 0 | 0 | 1.0 ± 0.1 | Rest |
| | 8 | 5.0 ± 0.6 | 300 ± 30 | 2.0 ± 0.2 | — |
| | 9 | 13.0 ± 7.0 | 780 ± 78 | 2.0 ± 0.2 | — |
| | 10 | 25.0 ± 3.0 | 1500 ± 150 | 2.0 ± 0.2 | — |
| | Total | | | 18.5 | — |
| CF | 1 | 60.0 ± 7.0 | 3600 ± 360 | 0.5 ± 0.5 | — |
| | 2 | 10.0 ± 7.0 | 600 ± 60 | 2.0 ± 0.2 | — |
| | 3 | 5.0 ± 0.6 | 300 ± 30 | 3.0 ± 0.3 | — |
| | 4 | 0 | 0 | 1.0 ± 0.1 | Rest |
| | 5 | 7.0 ± 7.0 | 438 ± 42 | 2.0 ± 0.2 | — |
| | 6 | 13.0 ± 7.0 | 780 ± 78 | 2.0 ± 0.2 | — |
| | 7 | 0 | 0 | 1.0 ± 0.1 | Rest |
| | 8 | 5.0 ± 0.6 | 300 ± 30 | 3.0 ± 0.3 | — |
| | 9 | 34.0 ± 7.0 | 2040 ± 204 | 2.0 ± 0.2 | — |
| | 10 | 34.0 ± 7.0 | 1080 ± 108 | 3.0 ± 0.3 | — |
| | Total | | | 19.5 | — |

According to some embodiments of the present invention, means and methods of accurately measuring the frequency characteristics of the FPPs are provided. It is a further purpose of the invention to provide means and methods of relaying the aforementioned data to the microprocessor of the device, and to process the data, such that the operation of the device can be adjusted or calibrated or attenuated by the patient or doctor. Similarly, it is a core purpose of the invention to provide means and methods of accurately measuring the pressure amplitude of the FPPs. It is a further purpose of the invention to provide means and methods of relaying the aforementioned data to the microprocessor of the device, and to process the data, such that the operation of the device can be adjusted or calibrated or attenuated by the patient or doctor. It is a core purpose of the invention to provide means and methods of controlling pressure variations positively or negatively in order to improve treatment by means of the FPPs. It is a further purpose of the invention to provide means and methods of relaying the aforementioned data to the microprocessor of the device, and to process the data, such that the operation of the device can be adjusted or calibrated or attenuated by the patient or doctor.

According to some embodiments, a protocol of Fluid Pressure Pulses (FPPs) useful for improving a patient's wellness is herein disclosed. The aforementioned protocol comprises sequences of individual FPPs, which are possibly different from each other. The fluid pressure pulses are administered to said patient's airway. The invention comprises protocols which can be asynchronous or synchronous, i.e., delivered in a way which may be independent of the patient's natural inspiratory cycle, cardiac cycle or other physiological functions, or dependent upon them, respectively. The above mentioned protocol may further be administered to the mouth cavity of a patient at a predetermined frequency and pressure in a predetermined manner which may be synchronous or asynchronous.

It is further within provision of the invention to provide the aforementioned FPPs wherein said FPPs comprise a given pressure amplitude, volume, duration and waveform; and further wherein said sequences of FPPs comprise a given frequency and duration.

The applied Protocols of FPPs may be in some embodiments synchronous and in other embodiments asynchronous, thus sometimes oppose an exhalation, and sometimes reinforce an inhalation. The patient breathes normally, whilst receiving the FPPs on inspiration and exhalation. During inspiration the supplied FPPs are in the same direction as the air being breathed in, and during exhalation the FPPs meet resistance of the air being breathed out. Both circumstances have a therapeutic effect. The rates and nature of the applied FPPs are predetermined by certain protocols of the invention, which are designed to relieve specific cardiac, pulmonary and other related conditions. Furthermore, means and methods of the invention are disclosed to enable selection of any particular protocol suitable to any particular patient and the progress of that patient's disease process during the course of treatment. The present invention supplies fluid pressure pulses (FPP) to the mouth cavity of a patient at a predetermined frequency and pressure in a predetermined manner which is not dependent upon the natural breathing rate of the patient, but in other aspects of the invention, fluid pressure pulses (FPP) are supplied to the mouth cavity of a patient at a predetermined frequency and pressure in a predetermined manner which is dependent upon the natural breathing rate of the patient. Another aspect of the invention is that means are disclosed for determining and/or supplying the fluid pressure pulses (FPPs). The aforementioned FPPs are supplied in particular sequences, tailored to the requirements of the treatment. The FPPs are in fact sequences (predetermined in some cases or adapted following feedback in other cases) of discrete pressurized air packets of controlled frequency and pressures, produced by positively or negatively pressurized air directed into the patient airway, occluded by a shutter action which "chops" and interrupts the air stream. It is understood that by pressure here is measured with respect to ambient pressure, and that negative pressure therefore refers to pressure below ambient.

The pulses produced by the cutout shapes described above may be of almost unlimited form. As an example, a radial cutout will allow full pressure 'at once' with some inevitable delay and 'smearing' of the expected square wave due to diffusion. The resultant pressure waveform may be fit by the expression $$P(t) = P_0 \operatorname{erfc}\left(\frac{l^2}{Dt}\right)$$

where $P_0$ is a constant, D is the diffusion constant of air, t is the time, and l is the distance from pulsehaler to the point of measurement.

The FPPs may be of positive pressure relative to the ambient atmosphere, negative pressure relative to the ambient atmosphere or any dynamic combination thereof.

The sequenced flow of packets of air (the FPPs) are facilitated into the airway of the patient, in a precise sequence, combination and manner (Protocol, exemplified in table 1), which is determined e.g., by the disease or symptom to be treated. FIG. 29 illustrates schematically, and for exemplary purposes only, several of such sequences of FPPs. For example, 110 represent 4 FPPs of predetermined volume and pressure, separated by identical intervals. The boxes represent volumes of air at a certain pressure that is introduced into the patient's airway. Another sequence 120, comprises 3 FPPs separated by identical intervals, followed by a longer interval, then followed by another FPP. A further sequence, 130, is shown. The sequence of 130 comprises one FPP, followed by a long interval, followed by administration of 3 FPPs at short interval, then followed by a longer interval, followed by another FPP. The individual FPPs can themselves be amplitudinally modulated, as in 140. It can thus be seen that a myriad of protocols can be composed and administered to a patient by the means and methods of the present invention.

It is within provision of the invention that the device be provided with means for sensing the inhalation and exhalation stages of the subject's respiratory cycle. In this way, the device can provide a different sequence of FPPs on inhalation vs. exhalation. It is further within provision of the invention that different patient conditions be treated by different protocols, each of which may have one set of sequences of FPPs for use during inhalation, another set of sequences used during exhalation, and possibly a third set of sequences used during the intervals between inhalation and exhalation.

Devices for sensing of inhalation vs. exhalation will be well known to those skilled in the art, for example comprising pressure sensors, $CO_2$ sensors, NO sensors, and others.

It is herein acknowledged that in some embodiments of the present invention, the protocols comprise not only the aforementioned sequences of FPPs, but also means and methods are provided to contemporaneously or simultaneously deliver streams of air with predetermined oscillating frequency into the patients airway, which persist for periods of time throughout or partially throughout the FPP sequences that are being delivered. Such airstreams can be likened to the drone of a Scottish bagpipe which produces a continuous stream of vibrating air at a predetermined frequency, whilst the chanter of the bagpipe produces the tune or melody. Certain particular predetermined oscillating frequencies of the aforementioned persistent streams of air are useful in stimulating NO production in certain tissues, promoting gas exchange and other therapeutically useful effects. Thus, some of the protocols of the invention will include the delivery of these drone-like vibrating airstreams in parallel to the predetermined sequences of FPPs.

The protocols exert their effects at the body organ level (e.g., lungs), the tissue level (e.g., bronchial smooth muscle relaxation, gas exchange at the alveolar membrane level), the cellular level (e.g., stimulation of epithelial NO production at the cellular level), the nervous system, parasympathetic nervous system, sympathetic nervous system, and others. There are several interrelated modes of interaction between the FPPs, including the setting up of resonating frequencies and harmonics with the natural resonances of different tissues.

An important facet of the invention is that means and methods are provided to design and implement any protocol for disease, based on sequences of FPPs. This is done by accumulating data from subjects provided with appropriate physiological sensors. In some embodiments the data will be fed back to fine tune the designed protocol. Protocols of the invention include particular frequencies and multiple harmonics or overtones thereof and are envisaged to cover the whole of relevant frequencies.

Mechanical resonance is the tendency of a mechanical system to absorb more energy when the frequency of its oscillations matches the system's natural frequency of vibration (its resonance frequency or resonant frequency) than it does at other frequencies. It is herein acknowledged that some of the protocols of the present invention provide FPPs at the natural frequency of target tissues in the patient to facilitate the therapeutic effects of the treatment protocols.

It is within provision of the invention to provide effects currently achieved by conventional medicines, such as increased cardiac output, decreased arterial resistance, decreased capillary resistance, increase in vascular elasticity, and the like, increase/decrease in sympathetic/parasympathetic response, and the like.

It is within provision of the invention that clinical improvement can be attained during and/or after use of the device in a number of diseases and syndromes. The following is a partial list of such illnesses in which it is envisaged that the device may be of service:

Diseases :Lung diseases; Obstructive Lung Diseases; COPD; Asthma; Bronchitis; Restrictive Lung Diseases (e.g., asbestosis, radiation fibrosis, ARDS); Cystic Fibrosis; Upper Respiratory Tract Infection; Sinusitis; Pharyngitis; Laryngitis; Otitis Media; Lower Respiratory Tract Infections; Pneumonia; Lung tumors; Cardiovascular Diseases; Coronary heart disease; Cardiomyopathy (CM), e.g.: Hypertrophic CM; Dilated CM; Hypertensive CM; Congestive Heart Failure; Inflammatory heart disease; Endocarditis ;Myocarditis; Cardiac Arrhythmias, e.g.: Atrial fibrillation Atrial flutter; Supraventricular Tachycardia; A-V blocks; Systemic Hypertension; Pulmonary hypertension; Atherosclerosis; Atherosclerosis of the Carotid arteries; Sleep apnea; Fibromyalgia. It is further within provision of the invention that a number of biological responses can be attained through use of the device and the protocols mentioned above. The following is a partial list of such effects.

Biological Effects: Smooth muscle relaxation; Pain blocking; Nitric Oxide release; Angiogenesis Shear forces exerted on fibroblasts facilitate tissue regeneration; Relief of dyspnea (neural effect?) Blood circulation; Improved perfusion through diseased capillaries; Improved alveolar gas exchange; Sympathetic function, Parasympathetic function, Autonomic balance; General influence on the nerves system and function; Change the chemical balance; Improvement of poorly functioning natural processes.

Protocols for Inspiration and Expiration:

In some embodiments of the present invention, a sensor at an opening of the device detects inspiration and expiration and accordingly signals the controller. The controller selects, alters or changes the FPP protocol that will be provided to the patient according to the predetermined programme.

If, for example, the 34 Hz frequency widens the bronchioles during inspiration, and 5 Hz during expiration facilitates expectoration, the appropriate frequencies will be provided. As a result, the bronchioles are widened and expectoration is increased.

If, for example, FPPs provided at a frequency of 40 Hz improve blood circulation during inspiration, and gas exchange is improved during expiration upon application of 8 Hz FPPs, then those frequencies will be automatically selected. Such a therapeutic treatment will be beneficial, because one will have, for example, lowered pulmonary pressure and improved oxygenation.

PROTOCOLS FOR RESPIRATION, CHANGES IN PRESSURE AND CAPACITY

It is an embodiment of the present invention to provide and disclose sensors and methods of using them to detect gases exhaled during respiration which then transfer signals to the controller. The controller can alter and change the frequency or frequencies of the provided FPPs of the specific protocol or select a protocol at the beginning of treatment. The FPP supply to the patient's airway can be generated by Turbine-like devices, CPAP-like devices, BILEVEL like devices, breathing and respiration devices, assisted breathing and similar for inspiration and expiration. Similarly, it is envisaged that the FPPs of the applied protocols can be of positive pressure, negative pressure, or a combination of both. Means and methods of providing resistance and perturbations to the natural breathing patterns of an individual patient are herein provided with protocols. Means and methods of selecting and generating such FPP protocols characterized by supplying FPPs of various frequencies, pressures and other characteristics, tailored according to the patients condition at the beginning of the therapy and during it's progress are provided. Thus the invention herein disclosed provides a non limited solution to pulmonary, respiration related and critical care patients.

Table 2 is a more detailed example of selected protocols for Asthma treatment, COPD or CF. It should be noted that for each condition, a series of FPPs are administered of predetermined Hz and duration. The RPM in the table refers to the revolutions of the revolving disc of exemplary embodiments of the invention, but any convenient means of producing the FPP's can be employed and remain within the scope of the invention. It should further be noted that each protocol has a predetermined Hz and duration of the FPP application which is selected because they have been found to beneficially effect certain physiological characteristics such as blood circulation, mucus transport, gas exchange, Functional residual capacity and relaxation smooth muscles, mucus transport in the upper bronchial region, blood circulation, Functional/residual capacity.

The
Blood circulation*
mucus transport, gas exchange, Functional residual capacity **
relaxation smooth muscles, mucus transport upper bronchial, blood circulation, Functional/residual capacity***
Rest asterisks (*, , *) in table 2 designate the physiological characteristics aforementioned, yet many other characteristics are envisaged as aspects of the current invention, which will be applied by means and methods of the present invention.

TABLE 2

| Asthma | HZ | RPM | duration (minutes) | COPD Step | Hz | RPM | duration (minutes) | CF | HZ | RPM | duration (minutes) |
|---|---|---|---|---|---|---|---|---|---|---|---|
| 1 | 40* | 2400 | 1 | 1 | 40* | 2400 | 1 | 1 | 2400 | 2400 | 0.5 |
| 2 | 8** | 480 | 1.5 | 2 | 5** | 300 | 2 | 2 | 600 | 600 | 2 |
| 3 | 5** | 300 | 1.5 | 3 | 7** | 420 | 2 | 3 | 240 | 240 | 1.5 |
| 4 | 25*** | 1500 | 2.5 | 4 | 7.3** | 438 | 2 | 4 | 300 | 300 | 2 |
| 5 | 0 | 0 | 1 | 5 | 0 | 0 | 1 | 5 | 480 | 480 | 1.5 |
| 6 | 10** | 600 | 2 | 6 | 19*** | 1140 | 2 | 6 | 0 | 0 | 1 (Rest) |
| 7 | 13*** | 780 | 1.5 | 7 | 8** | 480 | 2 | 7 | 438 | 438 | 1.5 |
| 8 | 16*** | 960 | 2 | 8 | 25*** | 1500 | 2 | 8 | 360 | 360 | 1 |
| 9 | 7** | 420 | 1.5 | 9 | 0 | 0 | 1 | 9 | 780 | 780 | 2 |
| 10 | 0 | 0 | 1 | 10 | 10** | 600 | 2 | 10 | 0 | 0 | 1 (Rest) |
| 11 | 34*** | 2040 | 2.5 | 11 | 34*** | 2040 | 2 | 11 | 300 | 300 | 2 |
| 12 | 19*** | 1140 | 3 | 12 | 16*** | 960 | 2 | 12 | 2040 | 2040 | 2 |
| Total | | | 21 | 13 | | 3000 | 1 | 13 | 1080 | 1080 | 3 |
| | | | | total | | | 22 | total | | | 21 |

| minute | | % | minute | | % | minute | | % |
|---|---|---|---|---|---|---|---|---|
| 1 | * | 4.8 | 2 | * | 9.1 | 0.5 | * | 2.4 |
| 6.5 | ** | 31.0 | 10 | ** | 45.5 | 11.5 | ** | 54.8 |
| 11.5 | *** | 54.8 | 8 | *** | 36.4 | 7 | *** | 33.3 |
| 2 | Rest | 9.5 | 2 | Rest | 9.1 | 2 | Rest | 9.5 |

Examples for 16 breathing cycles (inhalation/exhalation) per minute total 8 minutes

| | | minute | | | | | | | | | | | | | | |
|---|---|---|---|---|---|---|---|---|---|---|---|---|---|---|---|---|
| | | 1 1 minute | | 2 1 minute | | 3 1 minute | | 4 1 minute | | 5 1 minute | | 6 1 minute | | 7 1 minute | | 8 1 minute |
| cycle | | Hz | | Hz | | Hz | | Hz | | Hz | | Hz | | Hz | | Hz |
| 1 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 2 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 3 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 4 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 5 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 6 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 7 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 8 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 9 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 10 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 11 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 12 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 13 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 14 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 15 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |
| 16 | in | 34 | in | 19 | in | 16 | in | 16 | in | 40 | in | 25 | in | 16 | in | 16 |
| | ex | 5 | ex | 7.3 | ex | 5 | ex | 5 | ex | 8 | ex | 5 | ex | 5 | ex | 5 |

TABLE 2-continued

| cycle | | minute | | | | | | | | | | | | | | |
|---|---|---|---|---|---|---|---|---|---|---|---|---|---|---|---|---|
| | | 1<br>1 minute<br>Hz | | 2<br>1 minute<br>Hz | | 5<br>1 minute<br>Hz | | 6<br>1 minute<br>Hz | | 5<br>1 minute<br>Hz | | 6<br>1 minute<br>Hz | | 5<br>1 minute<br>Hz | | 6<br>1 minute<br>Hz |
| 1 | in<br>ex | 34<br>5 | in<br>ex | 19<br>7.3 | in<br>ex | 40<br>8 | in<br>ex | 25<br>5 | In<br>Ex | 40<br>8 | in<br>ex | 25<br>5 | In<br>Ex | 40<br>8 | in<br>ex | 25<br>5 |
| 2 | in<br>ex | 34<br>5 | in<br>ex | 19<br>7.3 | in<br>ex | 40<br>8 | in<br>ex | 25<br>5 | In<br>Ex | 40<br>8 | in<br>ex | 25<br>5 | In<br>Ex | 40<br>8 | in<br>ex | 25<br>5 |

The above description has, in a non limited manner, described an Air Delivery Device (ADD) and protocols for the application of the aforementioned Fluid Pressure Pulses (FPPs) to the airways of patients in need. It is envisaged that a person skilled in the art will be able, by learning from the disclosure herein provided, to provide means and methods for treating a wide number of diseases, symptoms and conditions, itionally to COPD, Asthma and Cystic Fibrosis. Such diseases symptoms and conditions include: Sinustis, Nasal Congestion, Pneumonia, Emphysema, Interstitial fibrosis, Pulmonary hypertension or Sarcoidosis.

It is furthermore envisaged that the above mentioned ADD and protocols will be useful in improving a patient's condition as measured by parameters, indices and scales selected from the group consisting of mental and physical health, quality of life, lung function, drug uptake, heart function, cardio-vascular efficiency, pulmonary efficiency, lung volume, oxygen uptake, gas exchange, NO production, carbon monoxide diffusion or any combination thereof.

As further examples of possible protocols, we present below mathematical representations of protocols which represent pressure as a function of time. The mathematical representation of the pressure as a function of time may take the form of

TABLE 3

Therapeutic Protocol for cardiopulmonary system

| Step number | Main frequency Hz | Rpm of rotating disc | 1st Harmony Hz | 2nd Harmony Hz | 3rd Harmony Hz | Duration sec | Remarks |
|---|---|---|---|---|---|---|---|
| 1 | 39.0 ± 0.2* | 2340 | 78 | +++117 | +++156 | 55 | — |
| 2 | 13.5 ± 0.2** | 810 | &&27 | *40.5 | +54 | 112 | — |
| 3 | 7.5 ± 0.2 | 450 | &&15 | 22.5 | ++30 | 106 | — |
| 4 | 4.7 ± 0.21 | 282 | ****9.4 | **14.1 | +18.8 | 106 | — |
| 5 | Recovery | | | | | 30 | Rest |
| 6 | 19.0 ± 0.2+ | 1140 | *38 | +57 | &&&76 | 81 | |
| 7 | 25.5 ± 0.2++++ | 1530 | +51 | &&&76.5 | 102 | 68 | — |
| 8 | 33.3 ± 0.2++ | 1998 | +66.6 | 99.9 | +++133.2 | 59 | — |
| 9 | 50.0 ± 0.2 | 3000 | &100 | +++150 | 200 | 55 | |
| 10 | Recovery | | | | | 30 | Rest |
| 11 | 6.5 ± 0.2*** | 390 | **13 | 19.5 | 26 | 106 | — |
| 12 | 13.5 ± 0.2** | 810 | ++27 | *40.5 | 54 | 112 | — |
| 13 | 33.3 ± 0.2 | 1998 | +66.6 | 99.9 | +++133.2 | 106 | — |
| 14 | 4.7 ± 0.2*** | 282 | ****9.4 | **14.1 | +18.8 | 106 | |
| 15 | 19.0 ± 0.2+ | 1140 | *38 | 57 | &&&76 | 81 | |
| 16 | Recovery | | | | | 30 | Rest |
| 17 | 51.0 ± 0.2+ | 3060 | &102 | +++153 | &&204 | 55 | |
| 18 | 25.5 ± 0.2++++ | 1530 | +51 | &&&76.5 | &&102 | 68 | |
| total | | | | | | 1366 | |

Examples from the protocol:
Reduce the shortness of breath *
Reduce the mucus viscosity **
Increase the cough instinct ***
Moving the Respiratory Cilia ****
Changing parasympathetic/sympathetic balance +
Increase pulmonary gas exchange ++
Increase nitric oxide production +++
Increase the capillary function ++++
Relaxation the heart ventricles &
Enhance lungs\heart circulation &&
Enhance coronary, heart muscles perfusion &&& triangle waves, square waves, sine waves, and others, all possibly modulating one another. Thus for example possible pressure sequences include but are not limited to:

$$P(t) = A \sin^{-1}(\sin(\omega_1 t)) + B \times \theta(\sin(\omega_2 t)) + C$$

where θ(t) is the Heaviside step function, $$\theta(x) = \begin{cases} 1; & x \geq 0 \\ 0; & x < 0 \end{cases}$$

-continued $$P(t) = A\sin^{-1}(\sin(\omega_1 t)) + B \times \theta(\sin(\omega_2 t)) + C$$

$$P(t) = A\sin^{-1}(\sin(\omega_1 T)) + B\sin^{-1}(\sin(\omega_2 t)) + C$$

and others as will be obvious to one skilled in the art. The constants A, B, C, $\omega_1$, and $\omega_2$ are chosen for instance such that 0.01 Hz≤$\omega_1$≤1 Hz, 0.1 Hz≤$\omega_2$≤10 Hz, 10 mmHg≤A≤250 mmHg, 10 mmHg≤B≤250 mmHg , and −250 mmHg≤C≤250 mmHg. Change high herz to 250 Hz It is within provision of the invention to provide enhancement of sporting performance and/or post-event recuperation. Since the device has been clinically demonstrated to cause dramatic improvements in e.g. 6 minute walk tests (see below), it is likely that improvements in blood oxygen levels and the like due to use of the device will provide similar improvements in the realm of sport and recreation.

It is within provision of the invention that the protocols used in operation of the device provide specific levels of pressure based on the expiratory resistance of the subject.

According to some embodiments, table 3 below indicates a specific embodiment of the therapeutic protocols according to which the device of the present invention may be activated.

The invention claimed is:

1. A device useful for delivering drugs to a respiratory system of a user, said device comprising:
   a. an air controlling mechanism for controlling passage of air during inhalation or exhalation of said air;
   b. at least one drug storing container:
   c. a breath-operated mechanism having a flap movable by a breath flow into a position blocking egress of said drugs from said storing container at expiration phase and into a position allowing egress of said drugs from said storing container at inspiration phase;
   said air controlling mechanism is adapted to generate pressure pulses of Negative Pressure or Positive Pressure into said respiratory system during inspiration or expiration;
   wherein said air controlling mechanism is selected from a group consisting of a perforated disc driven by a breath-driven turbine wheel actuated by energy provided by inspiration of exhalation air flow, a spring driven perforated disc rotating independently of the respiratory cycle phase and a shutter member reciprocatively movable-by an eccentric-pivoted lever mechanism driven-by said breath-driven turbine wheel.

2. The device according to claim 1, wherein said device is adapted for delivery of powdered drug supplied in capsule form.

3. The device according to claim 1, wherein a perforated rotating disc allows passage of said air through the perforation within said disc and to block and unblock the passage of said air.

4. The device according to claim 1, wherein said air controlling mechanism comprises a motor driven disc wheel adapted for synchronization with said breath-operated_ mechanism.

5. The device according to claim 1, wherein said breath-operated mechanism comprises a drug releasing shutter for controlling release of said drugs from said container during the operation of said air controlling mechanism.

6. The device according to claim 1, wherein said device additionally comprises a fluid vibrator selected from the group consisting of a piezoelectric vibrator, an eccentric vibrator, a tuning fork vibrator and any combination thereof.

7. The device according to claim 6, wherein said fluid vibrator is located in the middle section of said device or proximally to the outlet of said container.

8. The device according to claim 6, wherein said container comprises a pressure generator for generating high pressure therein.

9. The device according to claim 1, wherein said device is adapted for use as a sinusitis inhaler for use with one or both nostrils.

10. The device according to claim 1, further comprising a ratchet and pawl mechanism adapted to activate said device by lifting a pawl by the user's teeth.

* * * * *